(12) United States Patent
Ye et al.

(10) Patent No.: US 12,239,393 B2
(45) Date of Patent: Mar. 4, 2025

(54) HARD STOP THAT PRODUCES A REACTIVE MOMENT UPON ENGAGEMENT FOR CANTILEVER-BASED FORCE SENSING

(71) Applicant: Intuitive Surgical Operations, Inc., Sunnyvale, CA (US)

(72) Inventors: Zhou Ye, Santa Clara, CA (US); Harsukhdeep Ratia, Foster City, CA (US); Ashwinram Suresh, San Jose, CA (US); Craig Tsuji, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 839 days.

(21) Appl. No.: 17/322,276

(22) Filed: May 17, 2021

(65) Prior Publication Data
US 2021/0353373 A1    Nov. 18, 2021

Related U.S. Application Data

(60) Provisional application No. 63/026,320, filed on May 18, 2020.

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/70* (2016.02); *A61B 90/03* (2016.02); *A61B 17/29* (2013.01);
(Continued)

(58) Field of Classification Search
CPC .................... A61B 2090/034; A61B 90/03
See application file for complete search history.

(56) References Cited

U.S. PATENT DOCUMENTS

| 4,299,230 A | 11/1981 | Kubota |
| 4,430,895 A | 2/1984 | Colton |

(Continued)

FOREIGN PATENT DOCUMENTS

| CN | 2772442 Y | 4/2006 |
| CN | 101721246 A | 6/2010 |

(Continued)

OTHER PUBLICATIONS

Hazel., "Comparing Strain Gage Measurements to Force Calculations in a Simple Cantilever Beam," Worcester Polytechnic Institute Major Qualifying Project, 39 pages (Jan. 27, 2016).
(Continued)

*Primary Examiner* — Herbert K Roberts

(57) ABSTRACT

A medical device includes a shaft, a beam, a hard stop structure, and a link. A proximal end portion of the beam is coupled to the distal end portion of the shaft and a distal end portion of the beam is coupled to the link. A strain sensor is on the beam. A hard stop structure includes a proximal end portion, a distal end portion, and first opposing stop surfaces. The proximal end portion of the hard stop structure is coupled to a distal end portion of the shaft, and the distal end portion of the hard stop structure is coupled to the link. The first opposing stop surfaces are positioned to limit a lateral range of motion of the distal end of the beam with reference to the proximal end of the beam in a first direction by the first stop surfaces contacting one another.

19 Claims, 28 Drawing Sheets

(51) Int. Cl.
*A61B 90/00* (2016.01)
*B25J 19/06* (2006.01)
*A61B 17/29* (2006.01)

(52) U.S. Cl.
CPC ... *A61B 2034/305* (2016.02); *A61B 2090/034* (2016.02); *A61B 2090/064* (2016.02); *A61B 2562/0261* (2013.01); *B25J 19/06* (2013.01)

(56) References Cited

U.S. PATENT DOCUMENTS

| | | |
|---|---|---|
| 4,799,752 A | 1/1989 | Carome |
| 5,599,348 A | 2/1997 | Gentelia et al. |
| 5,625,576 A | 4/1997 | Massie et al. |
| 5,723,826 A | 3/1998 | Kitagawa et al. |
| 5,784,542 A | 7/1998 | Ohm et al. |
| 5,855,583 A | 1/1999 | Wang et al. |
| 5,892,860 A | 4/1999 | Maron et al. |
| 6,197,017 B1 | 3/2001 | Brock et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,459,926 B1 | 10/2002 | Nowlin et al. |
| 6,494,882 B1 | 12/2002 | Lebouitz et al. |
| 6,594,552 B1 | 7/2003 | Nowlin et al. |
| 6,620,174 B2 | 9/2003 | Jensen et al. |
| 6,730,021 B2 | 5/2004 | Vassiliades, Jr. et al. |
| 6,817,974 B2 | 11/2004 | Cooper et al. |
| 6,994,708 B2 | 2/2006 | Manzo |
| 7,077,842 B1 | 7/2006 | Cosman, Jr. et al. |
| 7,083,571 B2 | 8/2006 | Wang et al. |
| 7,169,141 B2 | 1/2007 | Brock et al. |
| 7,935,130 B2 | 5/2011 | Williams |
| 8,016,818 B2 | 9/2011 | Ellis et al. |
| 8,306,656 B1 | 11/2012 | Schaible et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,602,288 B2 | 12/2013 | Shelton, IV et al. |
| 8,620,473 B2 | 12/2013 | Diolaiti et al. |
| 8,628,518 B2 | 1/2014 | Blumenkranz et al. |
| 8,771,270 B2 | 7/2014 | Burbank |
| 8,800,838 B2 | 8/2014 | Shelton, IV |
| 8,840,628 B2 | 9/2014 | Green et al. |
| 8,918,212 B2 | 12/2014 | Larkin et al. |
| 8,945,095 B2 | 2/2015 | Blumenkranz et al. |
| 9,028,494 B2 | 5/2015 | Shelton, IV et al. |
| 9,192,448 B2 | 11/2015 | Blumenkranz |
| 9,204,923 B2 | 12/2015 | Manzo et al. |
| 9,232,979 B2 | 1/2016 | Parihar et al. |
| 9,671,860 B2 | 6/2017 | Ogawa et al. |
| 9,707,684 B2 | 7/2017 | Ruiz et al. |
| 9,782,214 B2 | 10/2017 | Houser et al. |
| 9,817,019 B2 | 11/2017 | Blumenkranz et al. |
| 9,952,107 B2 | 4/2018 | Blumenkranz et al. |
| 10,085,809 B2 | 10/2018 | Blumenkranz et al. |
| 10,130,366 B2 | 11/2018 | Shelton, IV et al. |
| 10,201,365 B2 | 2/2019 | Boudreaux et al. |
| 10,219,874 B2 | 3/2019 | Yu et al. |
| 10,238,458 B2 | 3/2019 | Verner et al. |
| 10,365,295 B2 | 7/2019 | Blumenkranz et al. |
| 10,378,883 B2 | 8/2019 | Gifford et al. |
| 10,398,433 B2 | 9/2019 | Boudreaux et al. |
| 10,470,796 B2 | 11/2019 | Page et al. |
| 10,595,836 B2 | 3/2020 | Smaby et al. |
| 10,595,887 B2 | 3/2020 | Shelton, IV et al. |
| 10,653,435 B2 | 5/2020 | Shelton, IV et al. |
| 10,682,141 B2 | 6/2020 | Moore et al. |
| 10,791,908 B2 | 10/2020 | Au |
| 11,137,414 B2 | 10/2021 | Blumenkranz et al. |
| 2003/0045834 A1 | 3/2003 | Wing et al. |
| 2005/0096502 A1 | 5/2005 | Khalili |
| 2005/0119527 A1 | 6/2005 | Banik et al. |
| 2006/0235314 A1 | 10/2006 | Migliuolo et al. |
| 2007/0043338 A1 | 2/2007 | Moll et al. |
| 2007/0052496 A1 | 3/2007 | Niemeyer et al. |
| 2007/0078484 A1 | 4/2007 | Talarico et al. |
| 2007/0119274 A1 | 5/2007 | Devengenzo et al. |
| 2007/0151390 A1* | 7/2007 | Blumenkranz ............ G01L 5/22 |
| | | 74/490.06 |
| 2007/0156019 A1 | 7/2007 | Larkin et al. |
| 2007/0282358 A1* | 12/2007 | Remiszewski ....... A61B 1/0057 |
| | | 606/159 |
| 2008/0046122 A1 | 2/2008 | Manzo et al. |
| 2008/0065105 A1 | 3/2008 | Larkin et al. |
| 2008/0065111 A1 | 3/2008 | Blumenkranz et al. |
| 2008/0132893 A1 | 6/2008 | D'Amelio et al. |
| 2009/0021752 A1 | 1/2009 | Cohen et al. |
| 2009/0088774 A1 | 4/2009 | Swarup et al. |
| 2009/0157092 A1 | 6/2009 | Blumenkranz et al. |
| 2009/0324161 A1 | 12/2009 | Prisco |
| 2010/0036384 A1 | 2/2010 | Gorek et al. |
| 2010/0063478 A1 | 3/2010 | Selkee |
| 2010/0087835 A1 | 4/2010 | Blumenkranz et al. |
| 2010/0154578 A1 | 6/2010 | Duval |
| 2010/0210975 A1 | 8/2010 | Anthony, III et al. |
| 2010/0219388 A1 | 9/2010 | Schena |
| 2010/0298844 A1 | 11/2010 | Blumenkranz |
| 2010/0313679 A1 | 12/2010 | Larkin et al. |
| 2011/0071543 A1 | 3/2011 | Prisco et al. |
| 2011/0178477 A1 | 7/2011 | Morel et al. |
| 2011/0277775 A1 | 11/2011 | Holop et al. |
| 2011/0282356 A1 | 11/2011 | Solomon et al. |
| 2011/0295269 A1 | 12/2011 | Swensgard et al. |
| 2011/0295270 A1 | 12/2011 | Giordano et al. |
| 2012/0016362 A1 | 1/2012 | Heinrich et al. |
| 2012/0123441 A1* | 5/2012 | Au ........................ A61B 34/30 |
| | | 606/130 |
| 2012/0199632 A1* | 8/2012 | Spivey ............. A61B 17/07207 |
| | | 227/176.1 |
| 2012/0257208 A1 | 10/2012 | Andersen et al. |
| 2012/0310257 A1 | 12/2012 | Kuchenbecker et al. |
| 2013/0046317 A1* | 2/2013 | Blumenkranz ........ A61B 34/70 |
| | | 606/130 |
| 2013/0291654 A1* | 11/2013 | Blumenkranz ......... G01L 1/246 |
| | | 73/862.045 |
| 2014/0005662 A1 | 1/2014 | Shelton, IV |
| 2014/0005678 A1 | 1/2014 | Shelton, IV et al. |
| 2014/0005681 A1 | 1/2014 | Gee et al. |
| 2014/0005708 A1 | 1/2014 | Shelton, IV |
| 2014/0137667 A1 | 5/2014 | Blumenkranz et al. |
| 2014/0257333 A1 | 9/2014 | Blumenkranz |
| 2015/0135832 A1* | 5/2015 | Blumenkranz ........... G02B 6/34 |
| | | 73/514.26 |
| 2015/0150635 A1 | 6/2015 | Kilroy et al. |
| 2015/0374447 A1 | 12/2015 | Blumenkranz et al. |
| 2016/0216167 A1 | 7/2016 | Blumenkranz et al. |
| 2016/0346513 A1* | 12/2016 | Swaney ............. A61M 25/0138 |
| 2017/0007345 A1 | 1/2017 | Smith et al. |
| 2017/0071688 A1* | 3/2017 | Cohen ................... A61B 34/76 |
| 2017/0095234 A1* | 4/2017 | Prisco ................... A61B 34/20 |
| 2017/0165017 A1 | 6/2017 | Chaplin et al. |
| 2017/0172687 A1 | 6/2017 | Smith et al. |
| 2017/0215944 A1 | 8/2017 | Keffeler |
| 2017/0252096 A1 | 9/2017 | Felder et al. |
| 2018/0042689 A1 | 2/2018 | Mozdzierz et al. |
| 2018/0078249 A1* | 3/2018 | Stoy ................. A61B 17/00234 |
| 2018/0206904 A1 | 7/2018 | Felder et al. |
| 2019/0069966 A1 | 3/2019 | Petersen et al. |
| 2019/0094084 A1 | 3/2019 | Swinehart et al. |
| 2019/0125354 A1* | 5/2019 | Deck .................. A61B 17/1285 |
| 2019/0175188 A1 | 6/2019 | P V R |
| 2019/0201018 A1 | 7/2019 | Shelton, IV et al. |
| 2019/0223960 A1 | 7/2019 | Chaplin et al. |
| 2019/0223966 A1 | 7/2019 | Holop et al. |
| 2019/0336228 A1 | 11/2019 | Blumenkranz et al. |
| 2020/0046404 A1 | 2/2020 | Page et al. |
| 2020/0129261 A1 | 4/2020 | Eschbach |
| 2020/0278265 A1 | 9/2020 | Suresh |
| 2021/0022819 A1 | 1/2021 | Duque et al. |
| 2021/0045819 A1 | 2/2021 | Castillo et al. |
| 2021/0387337 A1* | 12/2021 | Langenfeld ............ B25J 9/1635 |

(56) References Cited

U.S. PATENT DOCUMENTS

| | | |
|---|---|---|
| 2021/0401523 A1 | 12/2021 | Suresh |
| 2023/0225817 A1 | 7/2023 | Ye et al. |
| 2024/0130812 A1 | 4/2024 | Suresh |

FOREIGN PATENT DOCUMENTS

| | | | |
|---|---|---|---|
| CN | 102166136 | A | 8/2011 |
| CN | 202105024 | U | 1/2012 |
| CN | 102697559 | A | 10/2012 |
| DE | 1147411 | B | 4/1963 |
| EP | 0590713 | A2 | 4/1994 |
| EP | 0624346 | A2 | 11/1994 |
| EP | 1704822 | A1 | 9/2006 |
| EP | 2362285 | A2 | 8/2011 |
| EP | 2431000 | A2 | 3/2012 |
| EP | 3549538 | A1 | 10/2019 |
| JP | 2007528238 | A | 10/2007 |
| KR | 100703861 | B1 | 4/2007 |
| KR | 20070037565 | A | 4/2007 |
| KR | 100778387 | B1 | 11/2007 |
| KR | 20140079470 | A | 6/2014 |
| WO | WO-2007143859 | A1 | 12/2007 |
| WO | WO-2009123891 | A1 | 10/2009 |
| WO | WO-2012166806 | A1 | 12/2012 |
| WO | WO-2014151952 | A1 | 9/2014 |
| WO | WO-2016018815 | A1 | 2/2016 |
| WO | WO-2017064303 | A1 | 4/2017 |
| WO | WO-2019099562 | A1 | 5/2019 |
| WO | WO-2020102774 | A1 | 5/2020 |
| WO | WO-2020102776 | A1 | 5/2020 |
| WO | WO-2020102778 | A1 | 5/2020 |
| WO | WO-2020102780 | A1 | 5/2020 |
| WO | WO-2021076765 | A1 | 4/2021 |
| WO | WO-2021097386 | A1 | 5/2021 |
| WO | WO-2021236505 | A1 | 11/2021 |

OTHER PUBLICATIONS

International Search Report and Written Opinion for Application No. PCT/US2019/061880, mailed on Mar. 16, 2020, 15 pages.
Mertmann M., et al., "Grippers for the Micro Assembly Containing Shape Memory Actuators and Sensors," Le Journal de Physique IV France 7 (1997), Conference C5, Supplement of Journal de Physique III of Nov. 1997, pp. C5-621-C5-626.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

HARD STOP THAT PRODUCES A REACTIVE MOMENT UPON ENGAGEMENT FOR CANTILEVER-BASED FORCE SENSING

CROSS-REFERENCE TO RELATED APPLICATIONS

This patent application claims priority to and the filing date benefit of U.S. Provisional Patent Application No. 63/026,320, filed May 18, 2020, entitled "HARD STOP THAT PRODUCES A REACTIVE MOMENT UPON ENGAGEMENT FOR CANTILEVER-BASED FORCE SENSING," which is incorporated by reference herein in its entirety.

BACKGROUND

The embodiments described herein relate to medical devices, and more specifically to instruments used for minimally invasive surgery. More particularly, the embodiments described herein relate to (i) medical devices that include strain sensors on a cantilever beam coupled to an end effector to measure strain on the beam as a result of a force applied to the end effector during a surgical procedure, and (ii) a hard stop structure that limits a range of motion of the beam beyond a preset bending angle, that produces a reactive moment upon reaching the preset bending angle, or that both limits the range of motion and produces a reactive moment.

Known techniques for Minimally Invasive Surgery (MIS) employ instruments to manipulate tissue that can be either manually controlled or controlled via hand-held or mechanically grounded teleoperated medical systems that operate with at least partial computer-assistance ("telesurgical systems"). Many known MIS instruments include a therapeutic or diagnostic end effector (e.g., forceps, a cutting tool, or a cauterizing tool) mounted on an optional wrist mechanism at the distal end of a shaft. During an MIS procedure, the end effector, wrist mechanism, and the distal end of the shaft are inserted into a small incision or a natural orifice of a patient to position the end effector at a work site within the patient's body. The optional wrist mechanism can be used to change the end effector's position and orientation with reference to the shaft to perform a desired procedure at the work site. In known instruments, motion of the instrument as a whole provides mechanical degrees of freedom (DOFs) for movement of the end effector and the wrist mechanisms generally provide the desired DOFs for movement of the end effector with reference to the shaft of the instrument. For example, for forceps or other grasping tools, known wrist mechanisms are able to change the pitch and yaw of the end effector with reference to the shaft. A wrist may optionally provide a roll DOF for the end effector, or the roll DOF may be implemented by rolling the shaft. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

Force sensing surgical instruments are known and together with associated telesurgical systems produce associated haptic feedback during a MIS procedure, which brings better immersion, realism, and intuitiveness to a surgeon performing the procedure. For effective haptics rendering and accuracy, force sensors are placed on a medical instrument and as close to the anatomical tissue interaction as possible. One approach is to include a force sensor unit having electrical strain sensors (e.g., strain gauges) at a distal end of a medical instrument shaft to measure strain imparted to the medical instrument. The measured strain can be used to determine the force imparted to the medical instrument and as input to produce the desired haptic feedback.

FIG. 1A shows one example of a known force sensor unit that includes a cantilever beam 810 attached between the instrument distal tip component 510 (e.g., in some cases a clevis or other wrist or end effector component) and the instrument shaft 410 that extends back to the mechanical structure. Strain sensors 830 are on the beam and are used to measure strain in X- and Y-directions (arbitrary Cartesian directions that are orthogonal to each other and to a longitudinal axis of the beam and instrument shaft). For example, the strain sensors can include full Wheatstone bridges (full-bridges). In some cases, the strain sensors are split into two sets, one on the distal end of the beam and the other on the proximal end of the beam in order to reject common-modes. Because the beam is secured to a distal portion of the instrument shaft, the strain sensors sense strain on the beam orthogonal to a longitudinal axis of the shaft. A force F (FIG. 1B) applied orthogonal to the beam (i.e., an X or Y force) is determined by subtracting strain measurements determined by the full-bridges at the proximal and distal end portions of that side face of the beam.

Some known force sensing medical instruments also include a protective shroud 901 that covers the strain sensors 830 and their associated wires during use. To ensure the beam 810 remains cantilevered for accurate force sensing, known protective shrouds are not directly coupled to the distal tip component 510. Instead, such protective shrouds are separate from the distal tip component to allow the beam to deflect relative to the shroud when the force F is applied (see FIG. 1B). In certain situations, however, the distal end of the shroud can contact the beam or the distal tip component, thereby limiting bending of the beam. FIG. 1B shows one example, in which the beam 810 is displaced in the X direction such that it contacts one side of the distal end of the shroud 901, which limits or prevents further bending of the beam in the X direction by an amount that is dependent upon, for example, how rigid the shroud is and how much stiffer the shroud is compared to the beam.

Although limiting the displacement of the beam can advantageously prevent overload of the strain sensors 830, we have discovered that such known systems that engage the beam at a single point can cause a significant change in the strain distribution over the length of the beam 810. As a result, the strain sensors 830 produce signals that do not accurately represent the force F applied to the distal tip component. Specifically, we have discovered that in certain situations the contact between the distal end of the shroud 901 and the beam 810 (or the distal tip component 510) can cause distortion of the signals produced by the strain sensors 830. In certain situations, the distortion can cause the force sensed by the strain sensors 830 to be in the opposite direction of the force F actually applied to the distal tip component 510 (this phenomenon can be referred to as "force inversion").

FIGS. 2A and 2B show free body diagrams of example known force sensing medical instrument of FIGS. 1A and 1B to further illustrate this example of force distortion. As shown in FIG. 2A, the contact between the shroud and the beam can be modeled as a single point contact (at GND 2). In FIG. 2A, the distance L represents the distance from the base of the beam 810 (point GND 1) to the point where the shroud 901 contacts the beam 810 (point GND 2). The distance d represents the distance between the point where the shroud 901 contacts the beam 810 (point GND 2) and where the force F is applied to the distal tip component 510. FIG. 2B is a free-body diagram of the beam showing exaggerated deflection of the beam in such a condition as a result of the contact at point GND 2. As shown, we have discovered that the strain distribution along the top surface of the beam transitions from a region of compression to a region of tension, which causes the signals from the strain sensors 830 to inaccurately represent the applied force F. FIG. 2C shows the modeled forces with the beam "cut" at point GND 2 for purposes of analyzing the force and bending moment of the beam. FIG. 2C shows the reactive force $F_R$ produced by the single point contact, the effective force $F_E$, and the effective moment $M_E$ produced by the cantilever coupling to the shaft. By modeling the beam at the point of contact (at GND 2), the additional deflection (i.e., beyond this point of contact) can be considered as zero. Using the static and deflection equations shows that there are two different strain profiles over the entire beam length. The strain profile (ε) on the top side of the beam for the beam length l being between 0 and L is given by Eq. (1), where E is the modulus of elasticity of the beam and I is the moment of inertia of the XY cross-section of the beam:

$$\varepsilon(l) = -\frac{F_E(L-l)}{EI} + \frac{M_E}{EI} \qquad \text{Eq. (1)}$$

The strain profile (ε) on the top side of the beam for the beam length l being between L and L+d is given by Eq. (2):

$$\varepsilon(l) = -\frac{F(L+d-l)}{EI} \qquad \text{Eq. (2)}$$

Thus, at certain locations along the beam 810, the strain sensors 830 produce a signal associated with $F_E$ and not the actual force F. Because $F_E$ is acting in the opposite direction of the actual force F, the result is a distortion (and even an inversion of force direction) of the measured force. FIG. 3A is a graph showing the strain along the top of the beam 810 along the length of the beam based on Eq. (1) and Eq. (2) for the condition when the beam 810 contacts the shroud 910 at the single point of contact (GND 2). To further illustrate force distortion, FIG. 3B is a graph showing measured force (based on the strain signals) as a function of the actual force applied. As shown, when the beam is not in contact with the shroud, for example, when the actual force applied does not cause sufficient bending of the beam to result in contact, the relationship between the measured force and the actual force is linear, which allows for an accurate calibration (i.e., based on the slope of the line). At conditions where the beam is in contact with the shroud (as shown in FIG. 1B), however, the measured force decreases as the actual force increases. When the measured force is used to produce haptic feedback to a person operating an instrument that includes the beam (e.g., at a master controller), this measured force distortion and direction inversion problem can result in an undesirable positive feedback loop, which could cause unexpected or undesirable movement at the master controller.

Thus, a need exists for improved medical instruments that have force-sensing capabilities, and that can address the above-mentioned problems associated with force distortion and inversion.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, a medical device includes a shaft, a beam, a hard stop structure, and a link. The beam includes a proximal end portion and a distal end portion. The proximal end portion of the beam is coupled to a distal end portion of the shaft and the distal end portion of the beam is coupled to the link. A strain sensor is on the beam. The hard stop structure includes a proximal end portion, a distal end portion, and a first set of stop surfaces. The proximal end portion of the hard stop structure is coupled to the distal end portion of the shaft, and the distal end portion of the hard stop structure is coupled to the link. The first set of stop surfaces is positioned to limit a lateral range of motion of the distal end of the beam with reference to the proximal end of the beam in a first direction by the first set of stop surfaces contacting one another.

In some embodiments, the hard stop structure includes a second set of stop surfaces; and the second set of stop surfaces are positioned to limit the range of motion of the distal end of the beam with reference to the proximal end of the beam in a second direction opposite the first direction by the second set of stop surfaces contacting one another. In some embodiments, the first set of stop surfaces and the second set of stop surfaces are located on a first side of the beam. In some embodiments, the first set of stop surfaces and the second set of stop surfaces are located on opposite sides of the beam.

In some embodiments, the hard stop structure includes a second set of stop surfaces, and the first set of stop surfaces and the second set of stop surfaces are located on opposite sides of the beam. The second set of stop surfaces are positioned to limit the range of motion of the distal end of the beam with reference to the proximal end of the beam in the first direction by the second set of stop surfaces contacting one another.

In some embodiments, the first set of stop surfaces and the second set of stop surfaces are formed in a wall of the hard stop structure. In some embodiments, the hard stop structure includes a laser-cut tube in which the first set of stop surfaces and the second set of stop surfaces are defined. In some embodiments, the hard stop structure includes a laser-cut tube in which the first set of stop surfaces and the second set of stop surfaces are defined by a single laser cut, and the single laser cut extends about the laser-cut tube in a spiral.

In some embodiments, the medical device includes an end effector mechanism, and the end effector mechanism comprises a link. In some embodiments, the medical device includes a wrist mechanism and the wrist mechanism comprises the link.

In some embodiments, a medical device includes a shaft that comprises a proximal end portion and a distal end portion, a beam that comprises a proximal end portion and a distal end portion, a hard stop structure, and a link. The proximal end portion of the beam is coupled to the distal end portion of the shaft, and a distal end portion of the beam is coupled to the link. A strain sensor is on the beam and is configured to produce a signal associated with a strain in the beam that results when a force is exerted on the link. The hard stop structure comprises a proximal end portion coupled to the distal end portion of the shaft, and a distal end portion that is coupled to the link. The hard stop structure further comprises a first pair of stop surfaces on a first side of the beam and a second pair of stop surfaces on a second side of the beam that is opposite the first side. The first pair of stop surfaces are in contact with each other and the second pair of stop surfaces are in contact with each other when the strain in the beam exceeds a preset amount.

In some embodiments, the hard stop structure includes a wall and multiple interlocking components formed by an opening defined by a wall of the hard stop structure. The multiple interlocking components include the first pair of stop surfaces and the second pair of stop surfaces. In some embodiments, the hard stop structure includes a wall having a cylindrical shape, and the first pair of stop surfaces and the second pair of stop surfaces are formed by an opening defined by the wall of the hard stop structure, and the opening extends circumferentially around the wall by more than one revolution. In some embodiments, the opening forms a spiral of at least two revolutions.

In some embodiments, the first pair of stop surfaces and the second pair of stop surfaces produce a reactive moment when the hard stop structure is displaced by a preset bending angle. In some embodiments, the contact between first pair of stop surfaces and the contact between the second pair of stop surfaces produces a reactive moment acting on the beam. In some embodiments, the shaft includes a center axis between the proximal end portion of the shaft and the distal end portion of the shaft and the first pair of stop surfaces and the second pair of stop surfaces limit the displacement of the beam relative to the center axis to a threshold bending angle when the force is exerted on the link.

In some embodiments, the strain sensor is a first strain sensor on the beam at the proximal end portion of the beam, and the medical device further includes a second strain sensor on the beam at the distal end portion of the beam.

In some embodiments, a medical device includes a shaft, a beam, a hard stop structure, and a link. The shaft comprises a proximal end portion and a distal end portion and a center axis extending between the proximal end portion and the distal end portion. A proximal end portion of the beam is coupled to the distal end portion of the shaft and a distal end portion of the beam is coupled to the link. A strain sensor is on the beam and is configured to produce a signal associated with a strain in the beam that results when a force is exerted on the link. The hard stop structure comprises a proximal end portion, a distal end portion, and a lumen between the proximal end portion of the hard stop structure and the distal end portion of the hard stop structure. The proximal end portion of the hard stop structure is coupled to the distal end portion of the shaft, and the distal end portion of the hard stop structure is coupled to the link. The beam is at least partially within the lumen of the hard stop structure. The hard stop structure further comprises multiple interlocking components on a wall of the hard stop structure. The interlocking components limit the displacement of the beam relative to the center axis when the strain in the beam exceeds a preset amount.

In some embodiments, the multiple interlocking components are formed by an opening defined by the wall of the hard stop structure. In some embodiments, the hard stop structure has a cylindrical shape, and the multiple interlocking components are formed by an opening defined by the wall of the hard stop structure, and the opening extends circumferentially around the wall by more than one revolution. In some embodiments, the opening forms a spiral of at least two revolutions.

In some embodiments the multiple interlocking components include a first pair of stop surfaces on a first circumferential side of the hard stop structure and a second pair of stop surfaces on a second circumferential side of the hard stop structure. The second circumferential side being opposite the first circumferential side. The first pair of stop surfaces being in contact when the hard stop structure is displaced by a threshold displacement, and the second pair of stop surfaces being in contact when the hard stop structure is displaced by the threshold displacement. In some embodiments, the first circumferential side of the hard stop structure is in tension when the hard stop structure is placed by the threshold displacement, and the second circumferential side of the hard stop structure is in compression when the hard stop structure is placed by the threshold displacement.

In some embodiments, the multiple interlocking components include a first component that interlocks with a second component on a circumferential side of the hard stop structure. The first component includes a first stop surface and a second stop surface and the second component includes a first stop surface and a second stop surface. The first stop surface of the first component is in contact with the first stop surface of the second component when the force produces tension on the circumferential side of the hard stop structure, and the second stop surface of the first component is in contact with the second stop surface of the second component when the force produces compression on the circumferential side of the hard stop structure.

In some embodiments, the second stop surface of the first component is spaced apart from the second stop surface of the second component when the force produces tension on the circumferential side of the hard stop structure, and the first stop surface of the first component is spaced apart from the first stop surface of the second component when the force produces compression on the circumferential side of the hard stop structure. In some embodiments, the multiple interlocking components produce a reactive moment when the hard stop structure is displaced by a preset bending angle.

In some embodiments, a medical device includes a shaft, a beam, a hard stop structure, and a link. The shaft comprises a proximal end portion and a distal end portion and a center axis extending between the proximal end portion and the distal end portion. The beam comprises a proximal end portion coupled to the distal end portion of the shaft and a distal end portion coupled to a link. A strain sensor is on the beam and is configured to produce a signal associated with a strain in the beam that results when a force is exerted on the link. The hard stop structure comprises a proximal end portion, a distal end portion, and a lumen between the proximal end portion of the hard stop structure and the distal end portion of the hard stop structure. The proximal end portion of the hard stop structure is coupled to the distal end portion of the shaft, and the distal end portion of the hard stop structure is coupled to the link. The beam is at least partially within the lumen of the hard stop structure. The hard stop structure further comprises multiple interlocking components on a wall of the hard stop structure. The interlocking components produce a reactive moment when the strain in the beam exceeds a preset amount.

In some embodiments, the multiple interlocking components are formed by an opening defined by the wall of the hard stop structure. the hard stop structure has a cylindrical shape, the plurality of interlocking components is formed by an opening defined by the wall of the hard stop structure, the opening extending circumferentially around the wall by more than one revolution. In some embodiments, the opening forms a spiral of at least two revolutions. In some embodiments, multiple interlocking components include a first pair of stop surfaces on a first circumferential side of the hard stop structure and a second pair of stop surfaces on a second circumferential side of the hard stop structure with the second circumferential side being opposite the first circumferential side. The first pair of stop surfaces being in contact when the hard stop structure is displaced by a threshold displacement, and the second pair of stop surfaces being in contact when the hard stop structure is displaced by the threshold displacement.

In some embodiments, the first circumferential side of the hard stop structure is in tension when the hard stop structure is placed by the threshold displacement, and the second circumferential side of the hard stop structure is in compression when the hard stop structure is placed by the threshold displacement. In some embodiments, multiple interlocking components include a first component that interlocks with a second component on a circumferential side of the hard stop structure, the first component includes a first stop surface and a second stop surface and the second component includes a first stop surface and a second stop surface. The first stop surface of the first component is in contact with the first stop surface of the second component when the force produces tension on the circumferential side of the hard stop structure. The second stop surface of the first component is in contact with the second stop surface of the second component when the force produces compression on the circumferential side of the hard stop structure.

In some embodiments, the second stop surface of the first component is spaced apart from the second stop surface of the second component when the force produces tension on the circumferential side of the hard stop structure, and the first stop surface of the first component is spaced apart from the first stop surface of the second component when the force produces compression on the circumferential side of the hard stop structure. In some embodiments, the multiple interlocking components limit the displacement of the beam relative to the center axis to a preset bending angle when the force is exerted on the link.

In some embodiments, a medical device includes a shaft, a beam, a hard stop structure, and a link. The beam comprising a proximal end portion and a distal end portion. The proximal end portion of the beam being coupled to a distal end portion of the shaft. The link coupled to the distal end portion of the beam. A strain sensor is on the beam. The hard stop structure includes a proximal end portion, a distal end portion, and a plurality of pairs of opposing stop surfaces. The proximal end portion of the hard stop structure being coupled to the distal end portion of the shaft, and the distal end portion of the hard stop structure being coupled to the link. The plurality of pairs of opposing stop surfaces are positioned to limit a range of motion of the distal end of the beam with reference to the proximal end of the beam by one or more of the opposing stop surfaces contacting one another.

In some embodiments, a medical device includes a shaft, and an end effector coupled to a distal end of the medical device. The medical device further including means for sensing a lateral force applied to the end effector and means for limiting a lateral range of motion of the means for sensing the lateral force. The means for limiting the lateral range of motion comprising means for producing a reactive moment when the means for sensing the lateral range of motion has reached a preset range of motion. In some embodiments, the means for limiting the range of motion functions in all directions of the lateral force.

DETAILED DESCRIPTION

Figure 1A:
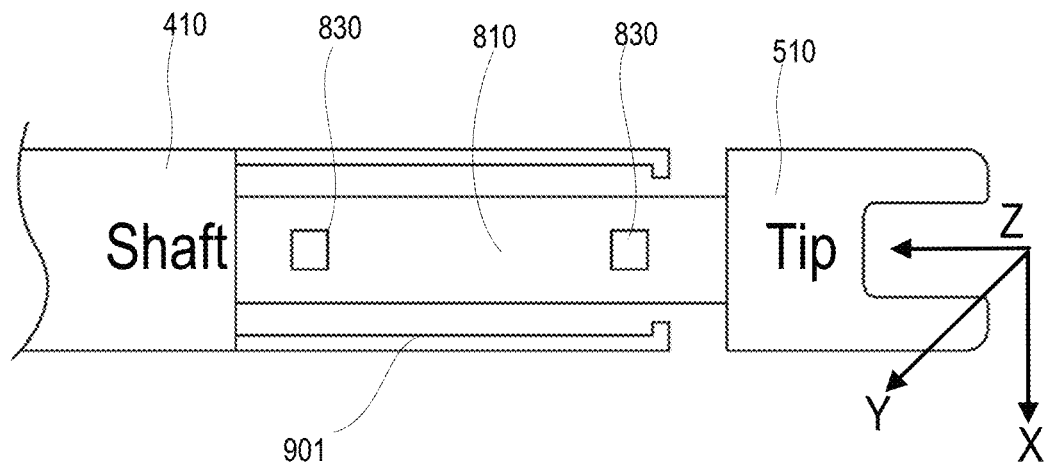
FIGS. 1A and 1B are diagrammatic illustration of a portion of a known medical device including a force sensor unit in a first configuration (FIG. 1A) and a second configuration (FIG. 1B).
Figure 1B:
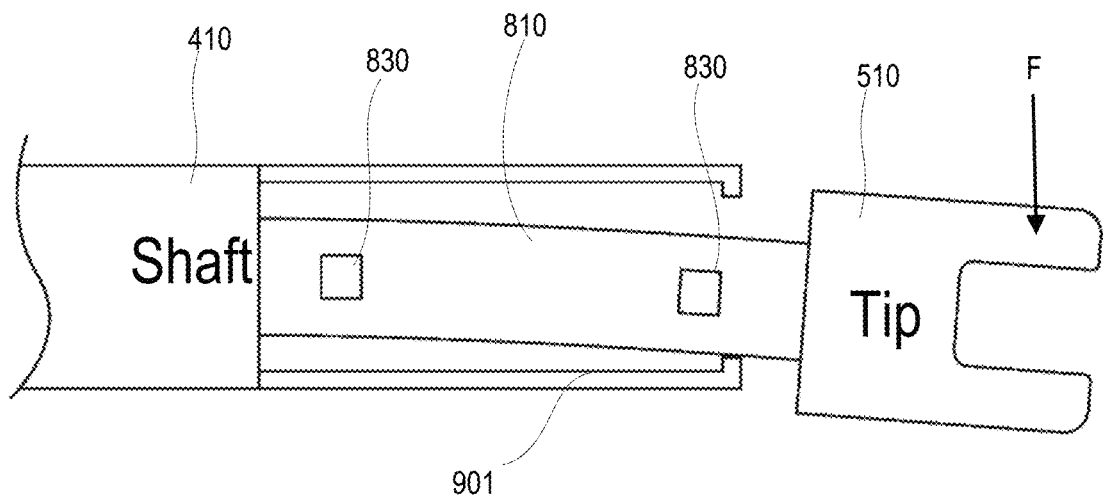
Figure 2A:
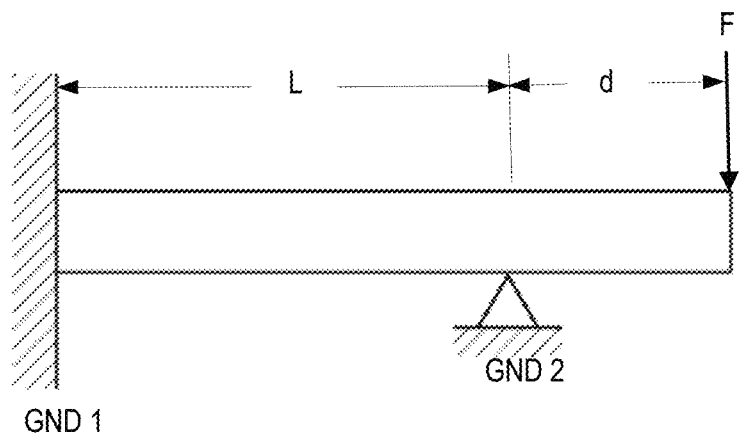
FIGS. 2A and 2B are free-body diagrams of the portion of the medical device shown in FIGS. 1A and 1B in the first configuration (FIG. 2A) and showing an exaggerated bending (FIG. 1B).
Figure 2B:
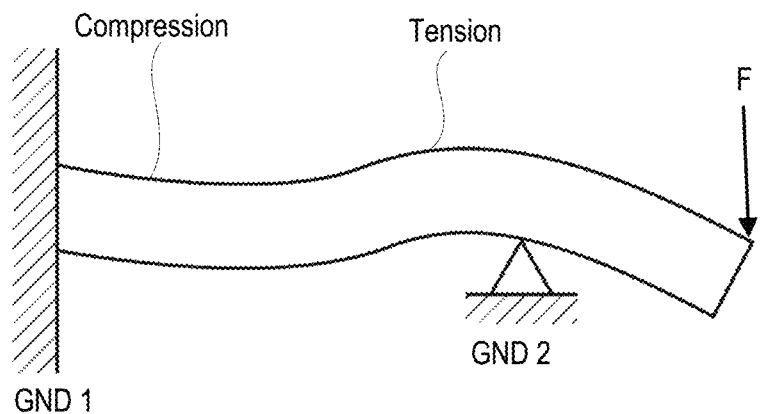
Figure 2C:
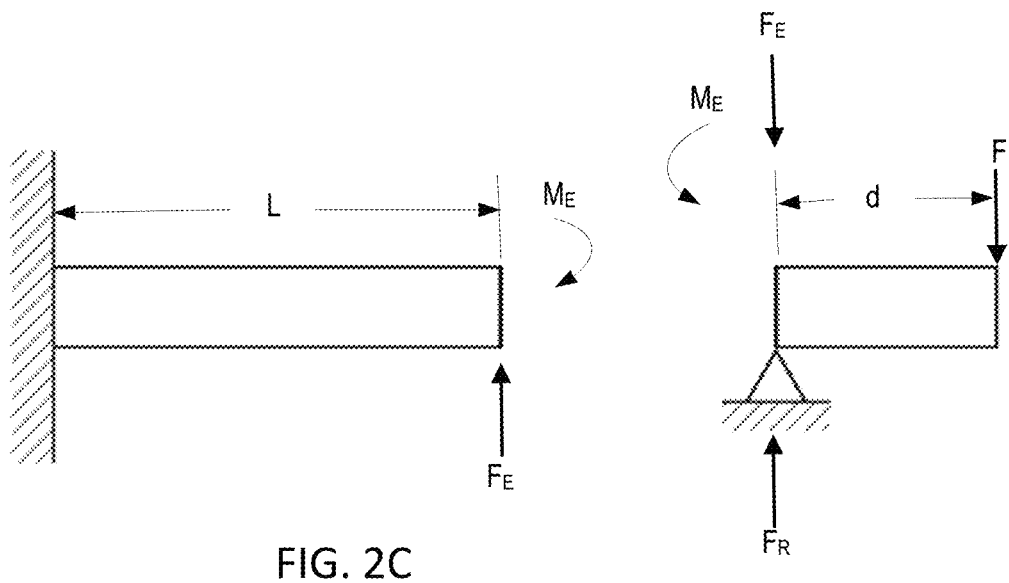
FIG. 2C is a free-body diagram of the portion of the medical device shown in FIGS. 1A and 1B being analyzed at a point of contact.
Figure 3A:
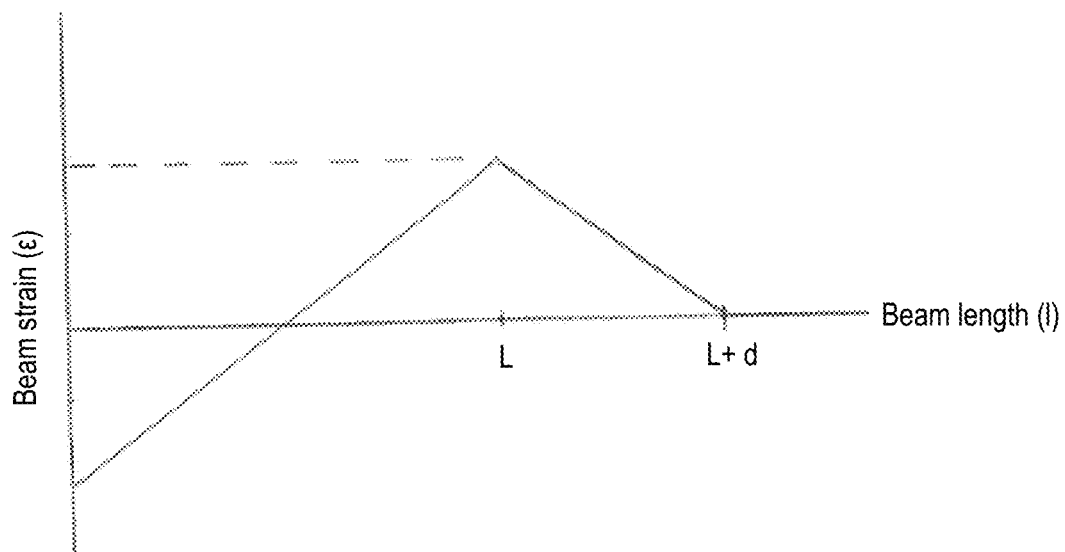
FIG. 3A is a graph showing the surface strain along the length of a beam of a force sensor unit when a single point of contact occurs.
Figure 3B:
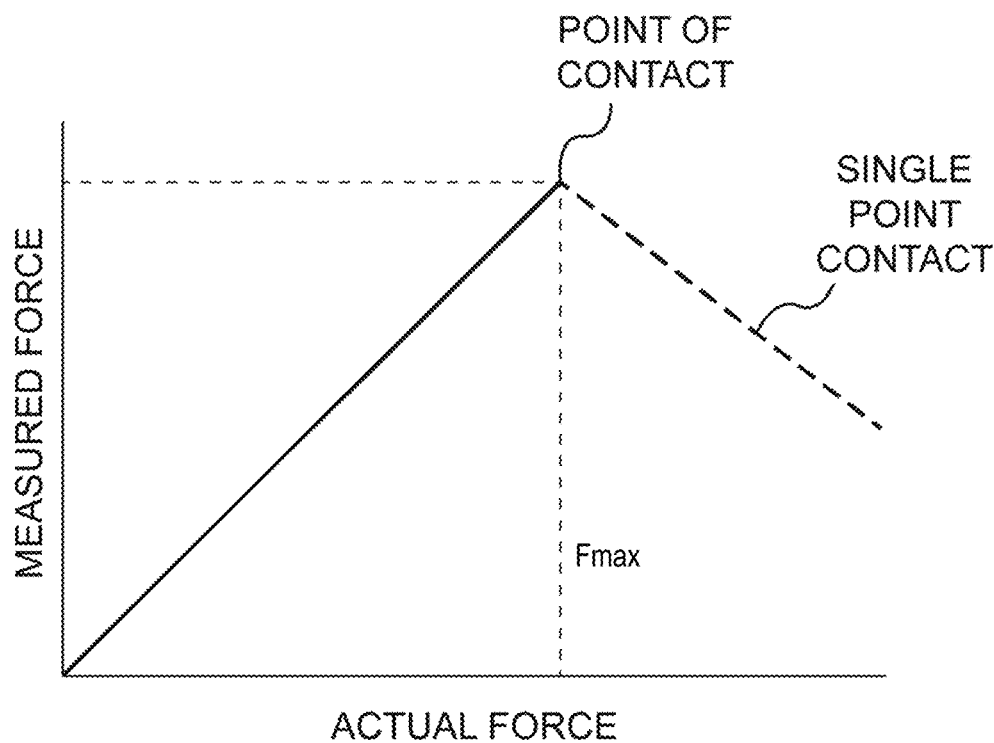
FIG. 3B is a graph showing the measured force (Y-axis) as a function of the actual force (X-axis) to demonstrate force distortion.

The embodiments described herein can advantageously be used in a wide variety of grasping, cutting, and manipulating operations associated with minimally invasive surgery. The medical instruments or devices of the present application enable motion in three or more degrees of freedom (DOFs). For example, in some embodiments, an end effector of the medical instrument can move with reference to the main body of the instrument in three mechanical DOFs, e.g., pitch, yaw, and roll (shaft roll). There may also be one or more mechanical DOFs in the end effector itself, e.g., two jaws, each rotating with reference to a clevis (2 DOFs) and a distal clevis that rotates with reference to a proximal clevis (one DOF). Thus, in some embodiments, the medical instruments or devices of the present application enable motion in six DOFs. The embodiments described herein further can be used to determine the forces exerted on (or by) a distal end portion of the instrument during use.

The medical instruments described herein include a force sensor unit having a cantilevered beam and one or more strain sensors on the beam. The medical devices include a hard stop structure that includes multiple opposing stop surfaces that can limit a range of motion of the beam when the opposing stop surfaces contact each other. For example, when a force imparted on a distal end of a medical instrument causes the distal end of the beam to bend or otherwise be displaced relative to a proximal end of the beam, the opposing stop surfaces of the hard stop structure can limit the range of motion of the beam. In some embodiments, the opposing stop surfaces of the hard stop structure can limit the range of motion of the beam in all directions of the lateral force imparted on a distal end portion of the medical instrument. In some embodiments, the hard stop structure includes a first set of stop surfaces and a second set of stop surfaces. In some embodiments, the first set of stop surfaces is disposed on the same side of the hard stop structure as the second set of stop surfaces. In some embodiments, the first set of stop surfaces is on an opposite side of the hard stop structure from the second set of stop surfaces.

In some embodiments, the hard stop structure includes multiple interlocking components that are formed by an opening cut into a wall of the hard stop structure. The interlocking components include multiple opposing stop surfaces as described above. In some embodiments, the opening in the hard stop structure (and interlocking components formed thereby) extend circumferentially around the hard stop structure in a spiral pattern. In some embodiments, the opening extends circumferentially around the wall of the hard stop structure by more than one revolution. In some embodiments, the opening extends circumferentially around the wall of the hard stop structure by at least two or more revolutions. In some embodiments, the hard stop structure is constructed of a stainless steel tube and the opening in the wall is laser cut.

The hard stop structure can be mounted to the same component of the medical instrument as the beam. The interlocking components formed by the opening defined in the wall of the hard stop structure enables the hard stop structure to bend flexibly to a relatively fixed preset angle or displacement. When the desired bend angle or displacement is reached, the interlocking components engage each other on at least one portion or one side of the hard stop structure and prevent the hard stop structure and the beam from bending further. For example, when the desired bend angle is reached, the opposing stop surfaces contact each other and prevent the hard stop structure and beam from bending further. In some embodiments, when the desired bend angle or displacement is reached, the interlocking components (i.e., the opposing stop surfaces of the interlocking components) prevent the hard stop structure and beam from bending or displacing further on both the compression side and the tension side of the hard stop structure and beam. Thus, in such an embodiment, the hard stop structure produces a reactive moment instead of a single reactive force once the hard stop engages.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California. such as, for example, the da Vinci Xi® Surgical System (Model IS4000), and the da Vinci X® Surgical System (Model IS4200). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

Figure 4:
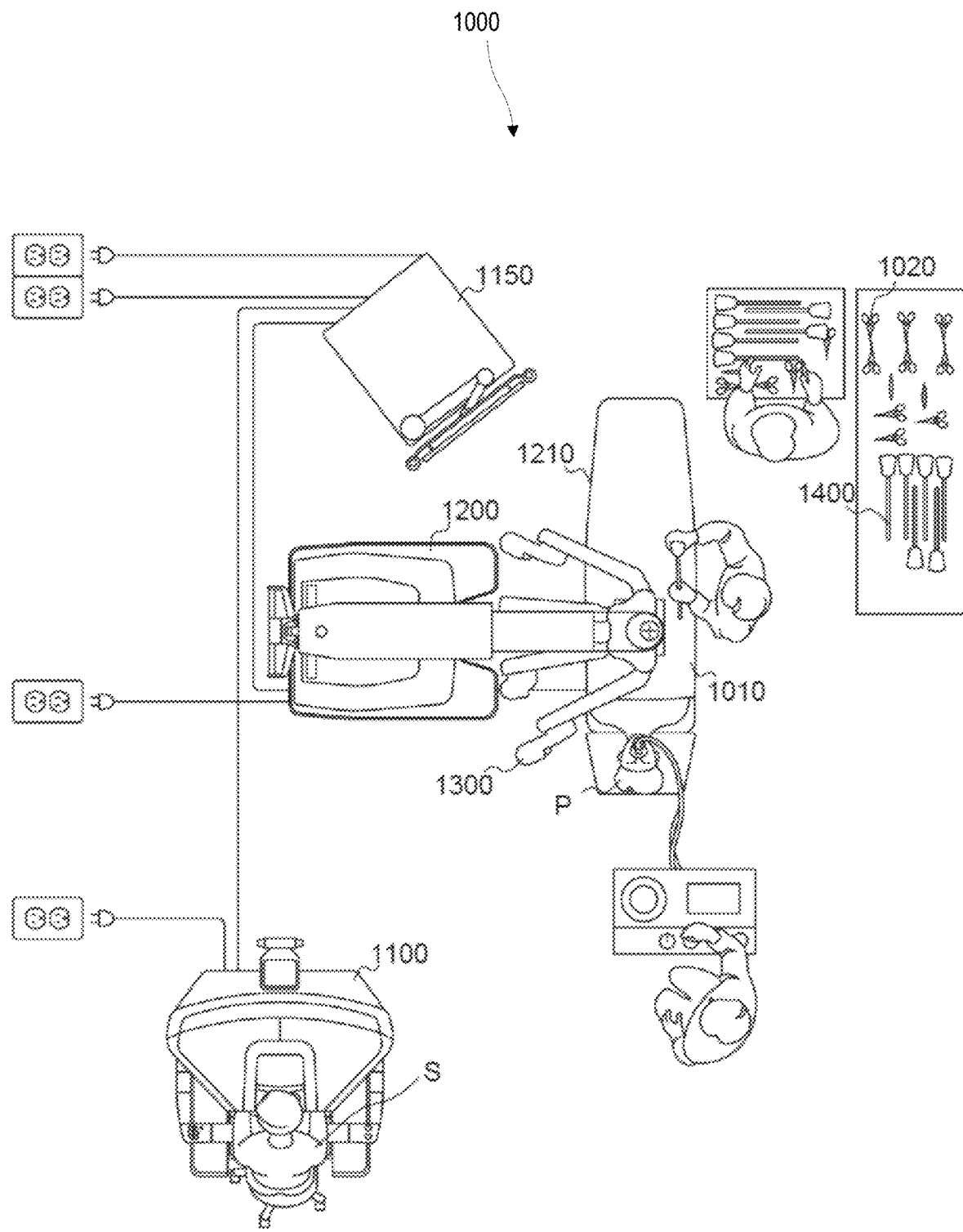
FIG. 4 is a plan view of a minimally invasive teleoperated medical system according to an embodiment being used to perform a medical procedure such as surgery.

FIG. 4 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled instruments 1400 through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 5:
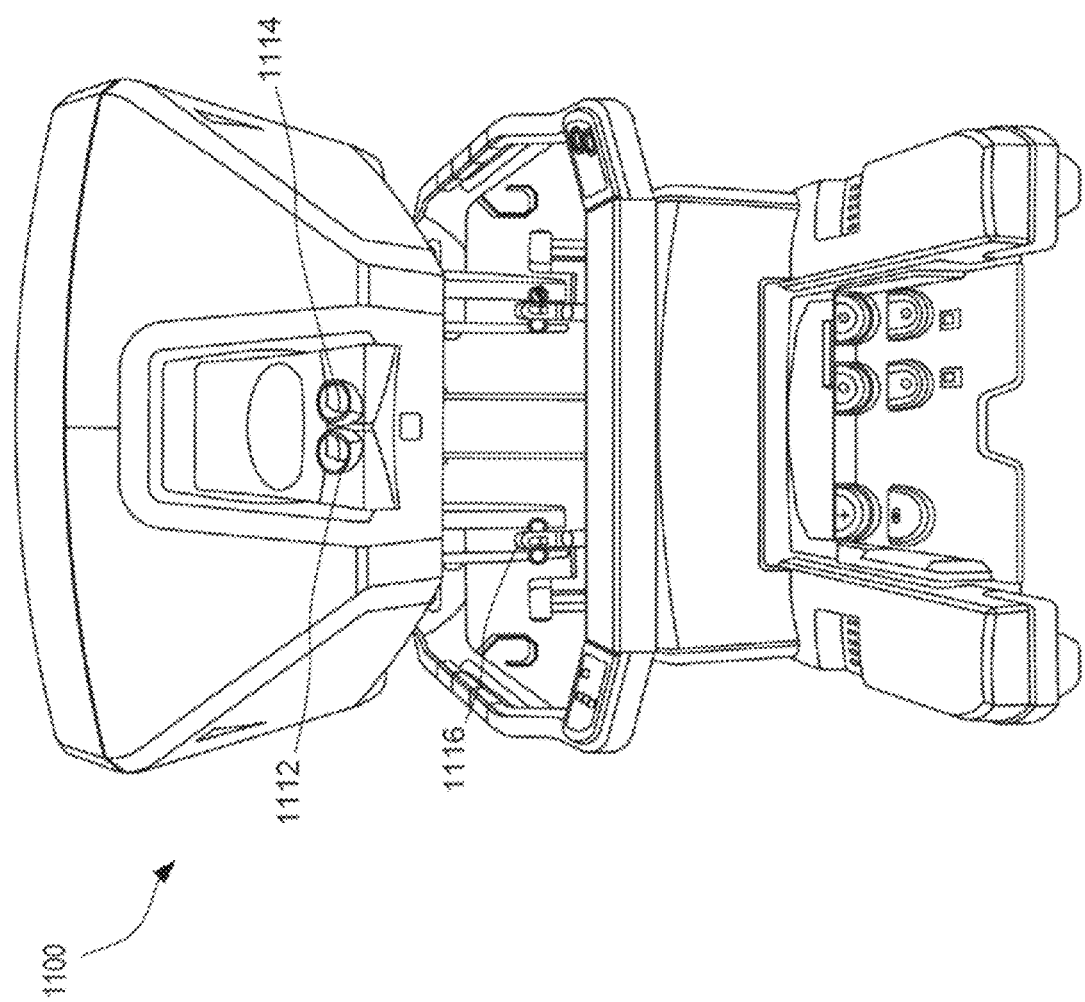
FIG. 5 is a perspective view of an optional auxiliary unit of the minimally invasive teleoperated surgery system shown in FIG. 4.

FIG. 5 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 4) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, strain and/or tactile feedback sensors (not shown) may be employed to transmit position, force, and tactile sensations from the instruments 1400 back to the surgeon's hands through the input control devices 1116.

The user control unit 1100 is shown in FIG. 4 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 6:
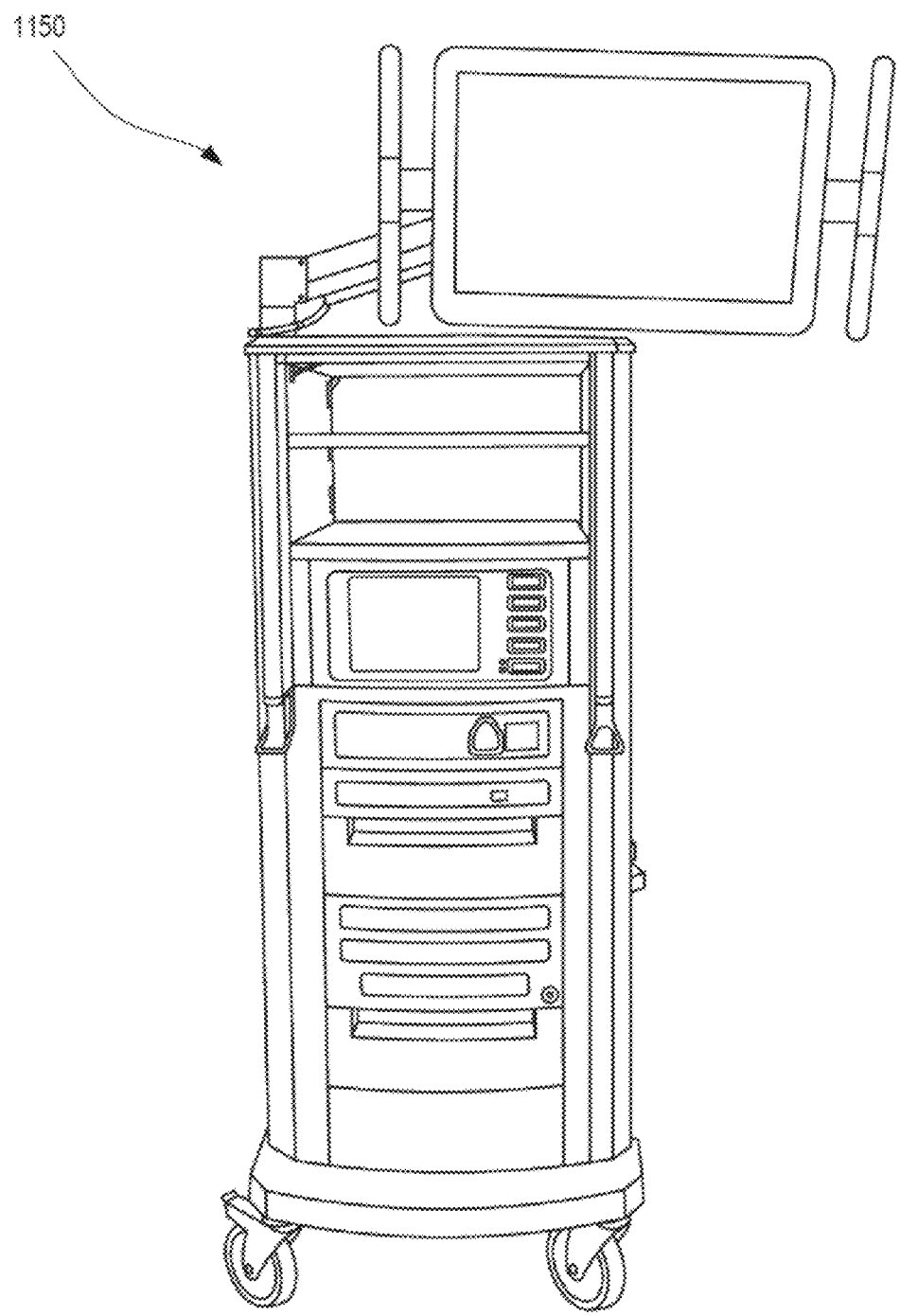
FIG. 6 is a perspective view of a user control console of the minimally invasive teleoperated surgery system shown in FIG. 4.

FIG. 6 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 7:
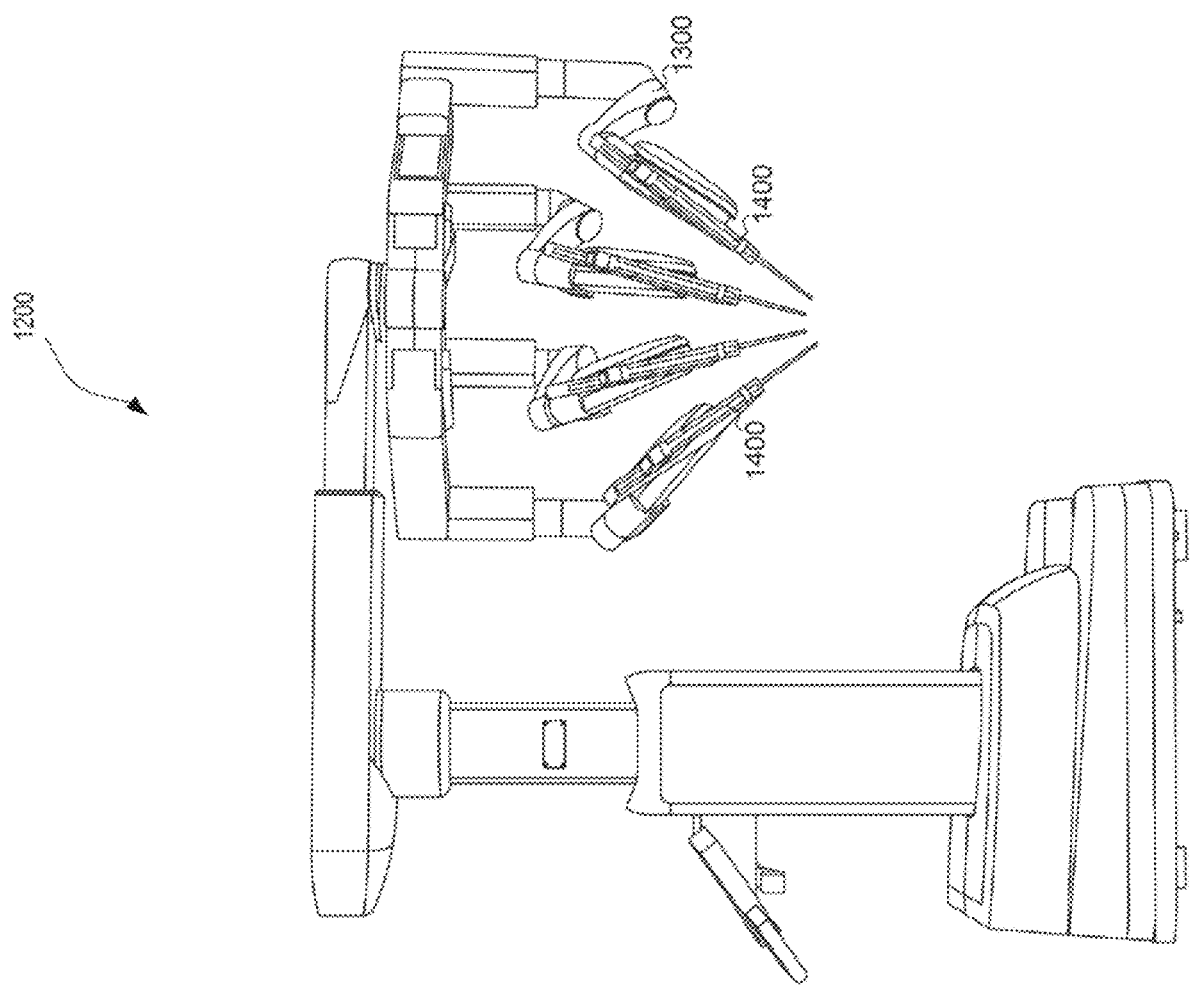
FIG. 7 is a front view of a manipulator unit, including a plurality of instruments, of the minimally invasive teleoperated surgery system shown in FIG. 4.

FIG. 7 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a software and/or kinematic remote center of motion is maintained at the incision or orifice. In this manner, the incision size can be minimized.

Figure 8A:
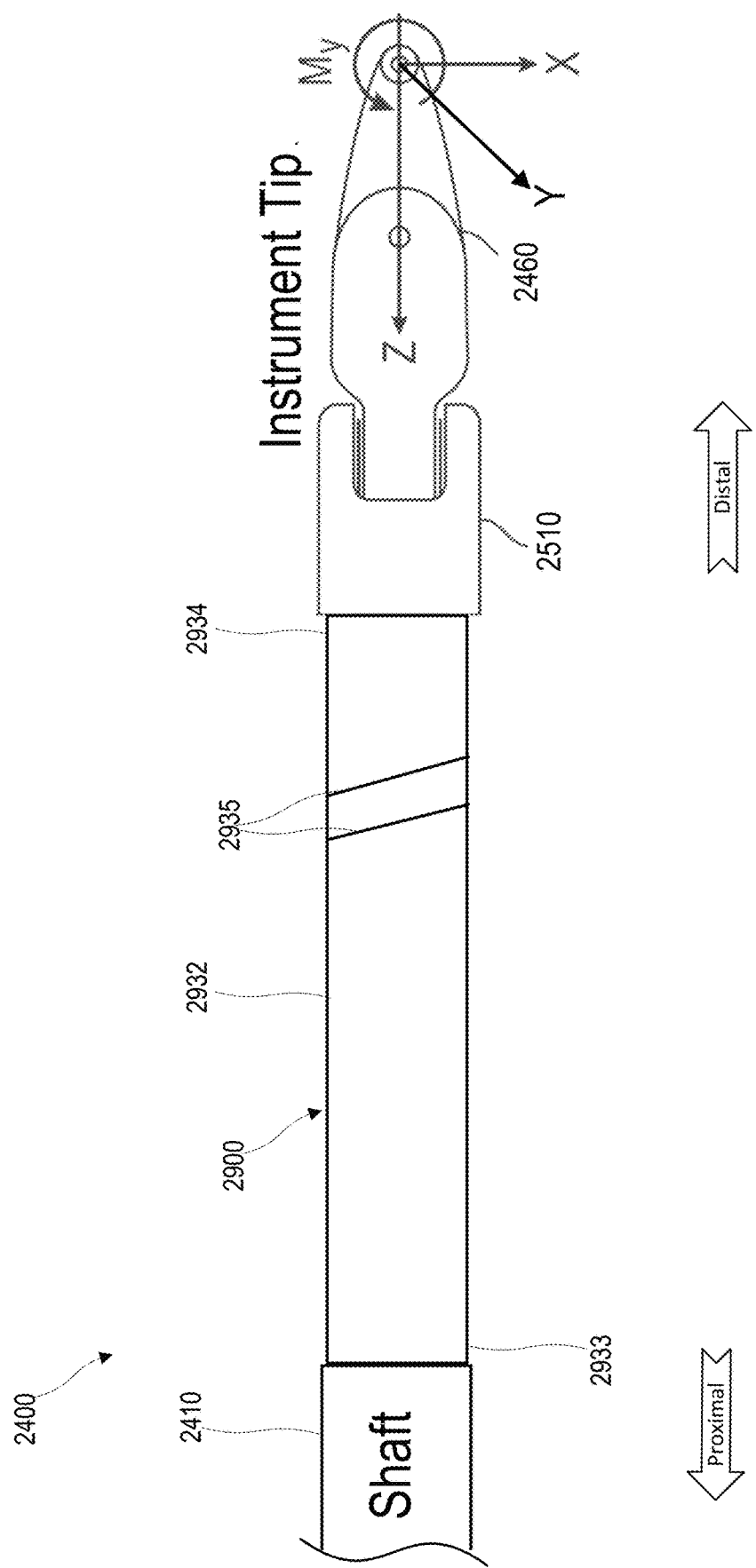
FIG. 8A is a diagrammatic illustration of a portion of a medical device including a force sensor unit, according to an embodiment.
Figure 8B:
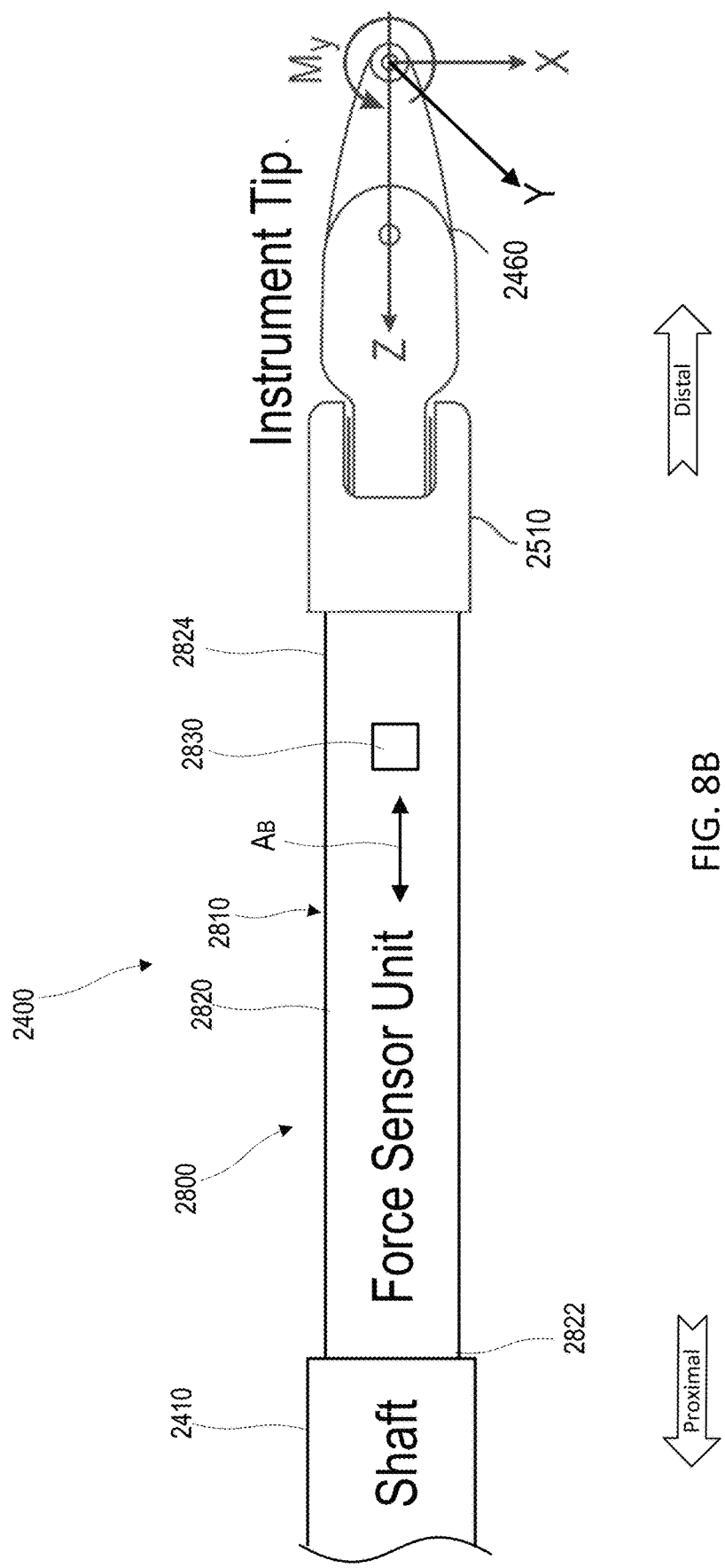
FIG. 8B is a diagrammatic illustration of the portion of the medical device of FIG. 8A with a hard stop structure removed from the device for illustration purposes.

FIGS. 8A and 8B are schematic illustrations of a portion of a distal end portion of a medical instrument 2400, according to an embodiment. The surgical instrument 2400 includes a shaft 2410, a hard stop structure 2900, a force sensor unit 2800 (see FIG. 8B) including a beam 2810, with one or more strain sensors (e.g., strain gauges) 2830 mounted on a surface along the beam 2810, and an end effector 2460 coupled at a distal end portion of the surgical instrument 2400. The end effector 2460 can include, for example, articulatable jaws or another suitable surgical tool that is coupled to a link 2510. In some embodiments, the link 2510 can be included within a wrist assembly having multiple articulating links. In some embodiments the link 2510 is included as part of the end effector 2460. As shown in FIG. 8B, the shaft 2410 includes a distal end portion that is coupled to a proximal end portion 2822 of the beam 2810. In some embodiments, the distal end portion of the shaft 2410 is coupled to the proximal end portion 2822 of the beam via another coupling component (such as an anchor or coupler, not shown). The shaft 2410 can also be coupled at a proximal end portion to a mechanical structure (not shown in FIGS. 8A and 8B) configured to move one or more components of the surgical instrument, such as, for example, the end effector 2460. The mechanical structure can be similar to the mechanical structure 7700 described in more detail below with reference to medical instrument 7400.

The hard stop structure 2900 includes a proximal end portion 2933, a distal end portion 2934, and a middle portion 2932 between the proximal end portion 2933 and the distal end portion 2934. In some embodiments, the hard stop structure 2900 defines an interior lumen (not shown in FIGS. 8A and 8B) in which the beam 2810 can be at least partially disposed. In some embodiments, the hard stop structure 2900 is cylindrical. In some embodiments, the hard stop structure 2900 is at least partially open along its length or around its circumference such that an interior of the hard stop structure 2900 can be viewed. As shown in FIGS. 8A and 8B, the proximal end portion 2933 of the hard stop structure 2900 is coupled to the shaft 2410 and the distal end portion 2934 of the hard stop structure 2900 is coupled to the link 2510. The proximal end portion 2933 can be fixedly coupled to the shaft 2410 and the distal end portion 2934 can be coupled to the link 2510 by any suitable mechanism, such as, for example, by a weld or an adhesive.

The hard stop structure 2900 also includes an opening 2935 (see FIG. 8A) defined by a wall of the hard stop structure 2900. For example, the opening 2935 can be cut into the wall of the hard stop structure 2900. In some embodiments, the opening 2935 can be laser cut into the wall of the hard stop structure 2900. The opening 2935 can define one or more sets of stop surfaces (not shown in FIGS. 8A and 8B). In some embodiments, the stop surfaces can be formed by or a part of one or more sets of interlocking components (not shown in FIGS. 8A and 8B) on the wall of the hard stop structure 2900. In some embodiments, the opening 2935 in the hard stop structure 2900 (and the sets of stop surfaces formed thereby) extends circumferentially around the hard stop structure 2900 in a spiral pattern. In some embodiments, the opening 2935 extends circumferentially around the wall of the hard stop structure 2900 more than one revolution. For example, as shown in FIG. 8A, the opening 2935 extends circumferentially around the hard stop structure 2900 by two revolutions. In some embodiments, the opening 2935 extends circumferentially around the wall of the hard stop structure 2900 by more than two revolutions. The hard stop structure 2900 can limit the displacement and relative movement of the beam relative to a center axis of the shaft 2410 and/or relative to a center axis $A_B$ of the beam 2810 (see FIG. 8B) when a strain in the beam 2810 exceeds a preset amount as described in more detail below. Further, in some embodiments, the hard stop structure 2900 can produce a reactive moment when the strain in the beam 2810 exceeds a present amount as described in more detail below.

As described above, the hard stop structure 2900 can prevent or limit the hard stop structure 2900 (and the beam 2810) from further bending or displacement when a desired preset bend angle or displacement is reached. Specifically, one or more sets of stop surfaces can contact each other to limit further displacement of the hard stop structure 2900. In some embodiments, the hard stop structure 2900 can include a set of stop surfaces on at least one portion or side of the hard stop structure 2900 that can prevent or limit further bending or displacement of the hard stop structure 2900 (and beam 2810). In some embodiments, the hard stop structure 2900 can include a set of stop surfaces on opposite sides of the hard stop structure 2900 (i.e., both the compression side and the tension side of the hard stop structure 2900) that can prevent further bending or displacement of the hard stop structure 2900 and beam 2820. Thus, in such an embodiment, the hard stop structure 2900 produces a reactive moment instead of a single reactive force once the stop surfaces engage each other. For example, when a force imparted on a distal end of the medical device 2400 causes the distal end of the beam 2810 to bend relative to a proximal end of the beam or relative to a center axis of the beam 2810 or shaft 2410, the opposing stop surfaces of the hard stop structure 2900 can limit the range of motion of the beam 2810. In some embodiments, the opposing stop surfaces of the hard stop structure 2900 can limit the range of motion of the beam in all directions of lateral force imparted on the distal end portion of the medical device.

The beam 2810 includes a middle portion 2820 (which functions as an active portion of the beam for force sensing), a proximal end portion 2822 and a distal end portion 2824. The beam 2810 defines a beam center axis $A_B$, which can be aligned within a center axis (not shown in FIGS. 8A and 8B) of the instrument shaft 2410. As shown, the strain sensor 2830 is coupled to the middle portion 2820 of the beam 2810. Thus, the middle portion 2820 functions as the active portion of the beam 2810 to sense strain on beam representative of the forces applied to the instrument 2400. Although shown as including only one strain sensor 2830, in other embodiments, the beam 2810 can include any number of strain sensors 2830 in various arrangements. The distal end portion 2824 of the beam 2810 is coupled to the end effector 2460 via a link 2510. In some embodiments, the link 2510 can be, for example, a clevis of the end effector 2460.

Generally, during a medical procedure, the end effector 2460 contacts anatomical tissue, which may result in X, Y, or Z direction forces being imparted on the end effector 2460 and that may result in moment forces such as a moment $M_Y$ about a y-direction axis as shown in FIGS. 8A and 8B. The one or more strain sensors 2830 (only one strain sensor 2830 is shown), which can be a strain gauge, can measure strain in the beam 2810 which can be used to determine the forces imparted on the end effector 2460 in the X and Y axes directions. These X and Y axes forces are transverse (e.g., perpendicular) to the Z axis (which is parallel or collinear with the center axis $A_B$). Such transverse forces acting upon the end effector 2460 can cause a bending of the beam 2810 (about either or both of the X axis or the Y axis), which can result in a tensile strain imparted to one side of the beam 2810 and a compression strain imparted to the opposite side of the beam 2810. The strain sensors 2830 on the beam 2810 can measure such tensile and compression strains.

Although shown as including only the force sensor unit 2800, in some embodiments, the instrument 2400 (or any of the instruments described herein) can include additional force sensor units to measure the axial force(s) (i.e., in the direction of the Z-axis parallel to the beam center axis $A_B$) imparted on the end effector 2460. An axial force sensor unit in an example surgical instrument can comprise a deflectable planar diaphragm sensor that deflects in response to a force. Alternatively, a deflectable ferrite core can be used within an inductive coil may be used or a or a fiber Bragg grating formed within an optical fiber can be used, for example. Other axial force sensor units may be used to sense a resilient axial displacement of the shaft 2410 (e.g., relative to the proximally mounted mechanical structure, not shown). An axial force $F_Z$ imparted to the end effector 2460 can cause axial displacement of the shaft 2410 in a direction along a center axis of the shaft (substantially parallel to the beam center axis $A_B$). The axial force $F_Z$ may be in the proximal direction (e.g., a reactive force resulting from pushing against tissue with the end effector) or it may be in the distal direction (e.g., a reactive force resulting from pulling tissue grasped with the end effector).

As described above, X and Y forces imparted on the end effector 2460 can result in strain in the beam 2810 when the beam 2810 is displaced (e.g., bent) relative to the center axis $A_B$ of the beam 2810 and thus relative to a center axis of the shaft 2410. Said another way, a distal end portion of the beam 2810 can bend relative to a proximal end portion of the beam 2810 such that the end portion of the beam is displaced a deflection distance relative to the center axis $A_B$. As described above, the hard stop structure 2900 can limit this displacement of the beam 2810 when a strain in the beam 2810 exceeds a preset amount. Further, in some embodiments, the hard stop structure 2900 can produce a reactive moment when the strain in the beam 2810 exceeds the preset amount and the hard stop structure 2900 is displaced by a preset bending angle. More specifically, the hard stop 2900 can include a first set of opposing surfaces that contact each other when the hard stop structure 2900 is in tension and displaced by a threshold displacement and a second set of opposing surfaces that are in contact when the hard stop structure 2900 is in compression and displaced by the threshold displacement. In such a case, the hard stop structure 2900 produces a reactive moment.

Figure 9A:
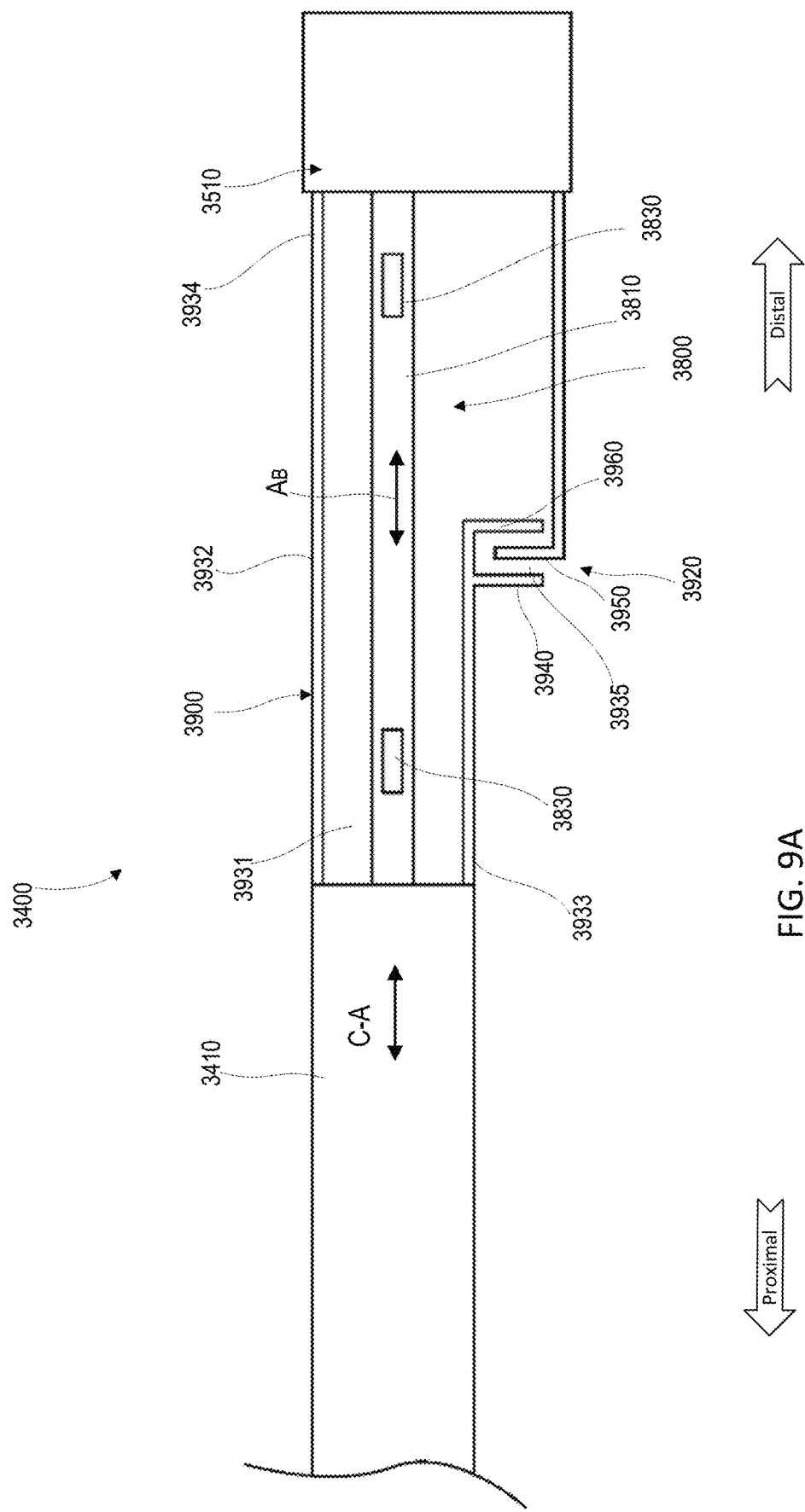
FIG. 9A is a diagrammatic illustration of a portion of a medical device including a force sensor unit and hard stop structure, according to an embodiment and shown in a first configuration.
Figure 9B:
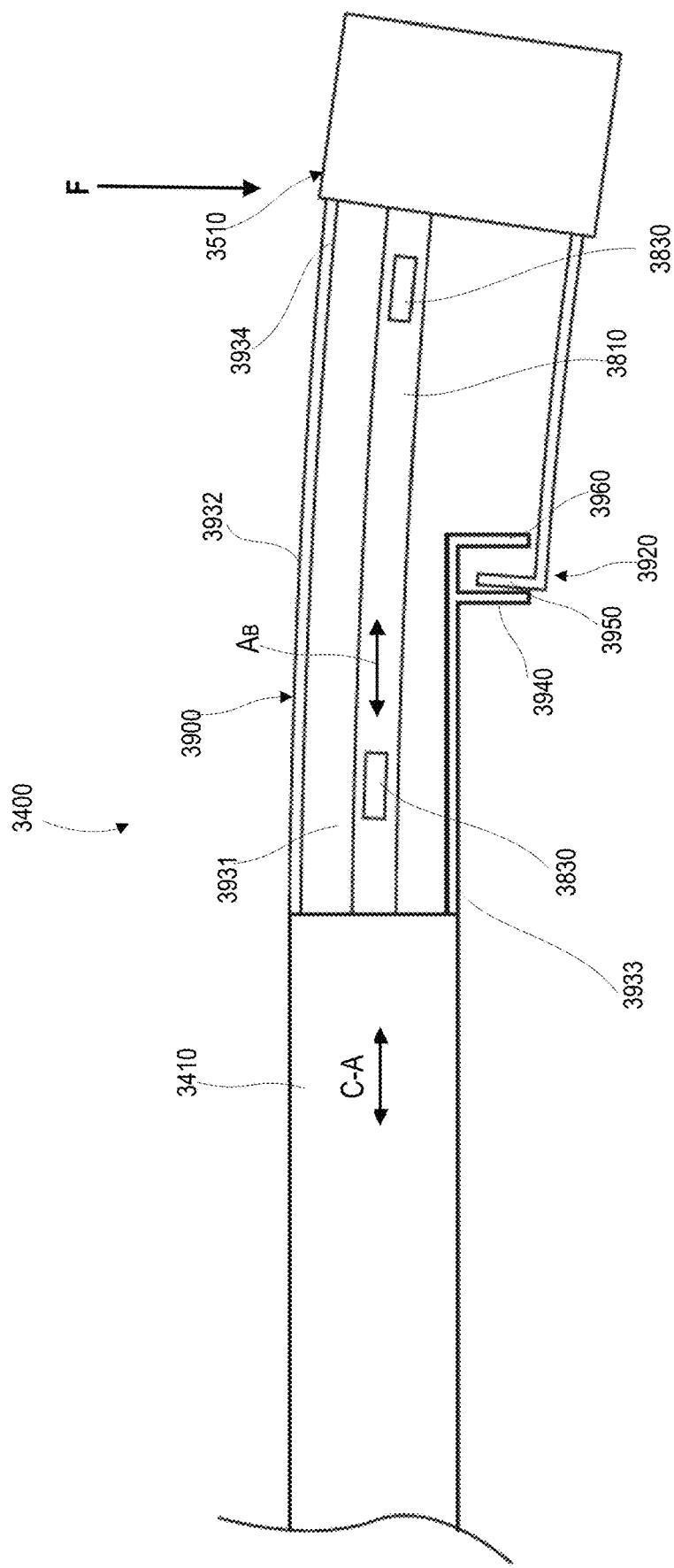
FIG. 9B is a diagrammatic illustration of the portion of the medical device of FIG. 6A shown in a second configuration when a force is exerted on a distal end portion of the medical device.

Although the hard stop structure 2900 is shown as including an opening 2935 that extends around at least a portion of the wall of the hard stop structure 2900, in other embodiments, a hard stop can include any suitable structure that includes one or more pairs of stop surface. For example, FIGS. 9A and 9B are schematic illustrations of a portion of a distal end portion of a medical instrument 3400, according to an embodiment. The surgical instrument 3400 includes a shaft 3410, a hard stop structure 3900, a force sensor unit 3800 including a beam 3810, and strain sensors (e.g., strain gauges) 3830 mounted on a surface along the beam 3810, and a link 3510 coupled at a distal end portion of the surgical instrument 3400. The link 3510 can be, for example, part of or coupled to an end effector (not shown) that can include, for example, articulatable jaws or another suitable surgical tool. In some embodiments, the link 3510 can be included within a wrist assembly having multiple articulating links. A proximal portion of the beam 3810 is coupled to the shaft 3410 and a distal portion of the beam 3810 is coupled to the link 3510. In some embodiments, the distal end portion of the shaft 3410 is coupled to the proximal portion of the beam 3810 via another coupling component (such as an anchor or coupler, not shown). The shaft 3410 can also be coupled at a proximal end portion to a mechanical structure (not shown in FIGS. 9A and 9B) configured to move one or more components of the surgical instrument. The mechanical structure can be similar to the mechanical structure 7700 described in more detail below with reference to medical instrument 7400.

The hard stop structure 3900 includes a proximal end portion 3933, a distal end portion 3934, and a middle portion 3932 between the proximal end portion 3933 and the distal end portion 3934. As shown in FIGS. 9A and 9B, the proximal end portion 3933 of the hard stop structure 3900 is coupled to the shaft 3410 and the distal end portion 3934 of the hard stop structure 3900 is coupled to the link 3510. The proximal end portion 3933 can be fixedly coupled to the shaft 3410 and the distal end portion 3934 can be coupled to the link 3510 by any suitable mechanism, such as, for example, by a weld or an adhesive. In this manner, displacement of the link 3510 relative to the shaft 3410 will cause displacement of the distal end portion 3934 of the hard stop structure 3900 relative to the proximal end portion 3933 of the hard stop structure 3900. The hard stop structure 3900 also includes a set of stop surfaces that limit a range of motion of the distal end of the beam 3810 (and the distal end portion 3934 of the hard stop structure 3900) with respect to the proximal end of the beam 3810 (and the proximal end portion 3933 of the hard stop structure 3900). Specifically, the hard stop structure 3900 includes an opening 3935 defined by a wall of the hard stop structure 3900. As shown in this embodiment, the opening 3935 defines a set of interlocking components 3920 including the components 3940, 3950 and 3960 on the wall of the hard stop structure 3900. In some embodiments, the opening 3935 in the hard stop structure 3900 and interlocking components 3940, 3950, 3960 can extend at least partially circumferentially around the hard stop structure 3900. For example, the opening 3935 can be cut into the wall of the hard stop structure 3900. In other embodiments, the opening 3935 in the wall and the interlocking components 3940, 3950, 3960 can be primarily on a single side of the hard stop structure 3900.

As described above for previous embodiments, the hard stop structure 3900 can limit the displacement of the beam 3810 relative to a center axis C-A of the shaft 3410 and/or relative to a center axis $A_B$ of the beam 3810 when a strain in the beam 3810 exceeds a preset amount. Said another way, the hard stop structure 3900 can limit the displacement or bending of the beam 3810 when the beam 3810 is displaced or bends a preset amount. More specifically, when a force F (shown in FIG. 9B) is imparted on a distal portion of the medical device (e.g., at link 3510) in the X or Y directions (see FIGS. 8A and 8B for reference to X, Y and Z directions), such transverse force can cause the beam 3810 to bend (about either or both of the X axis or the Y axis), which can result in a tensile strain imparted to one side of the beam 3810 and a compression strain imparted to the opposite side of the beam 3810. The strain sensors 3830 on the beam 3810 can measure such tensile and compression strains. As the beam 3810 bends to a preset bending angle, a surface of the component 3950 will contact a surface of the component 3940 and limit further movement of the beam 3810 as shown in FIG. 9B. The opposing surfaces of the components 3950 and 3940 thus function as a set of stop surfaces to prevent the hard stop structure 3900 and the beam 3810, which is coupled to the same components of the medical device (i.e., the link and the shaft) from further displacement or bending.

Figure 10A:
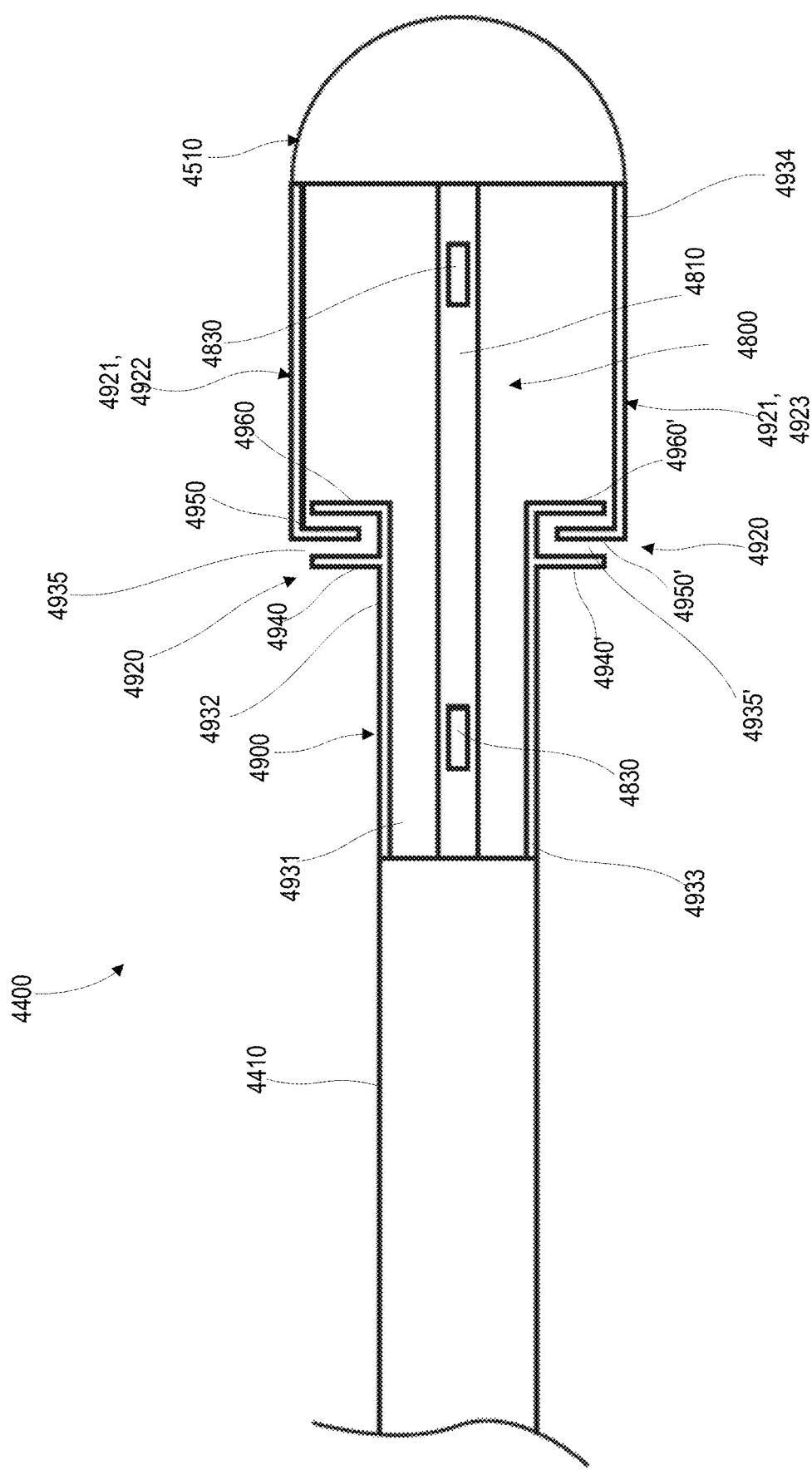
FIG. 10A is a diagrammatic illustration of a portion of a medical device including a force sensor unit and hard stop structure, according to an embodiment and shown in a first configuration.
Figure 10B:
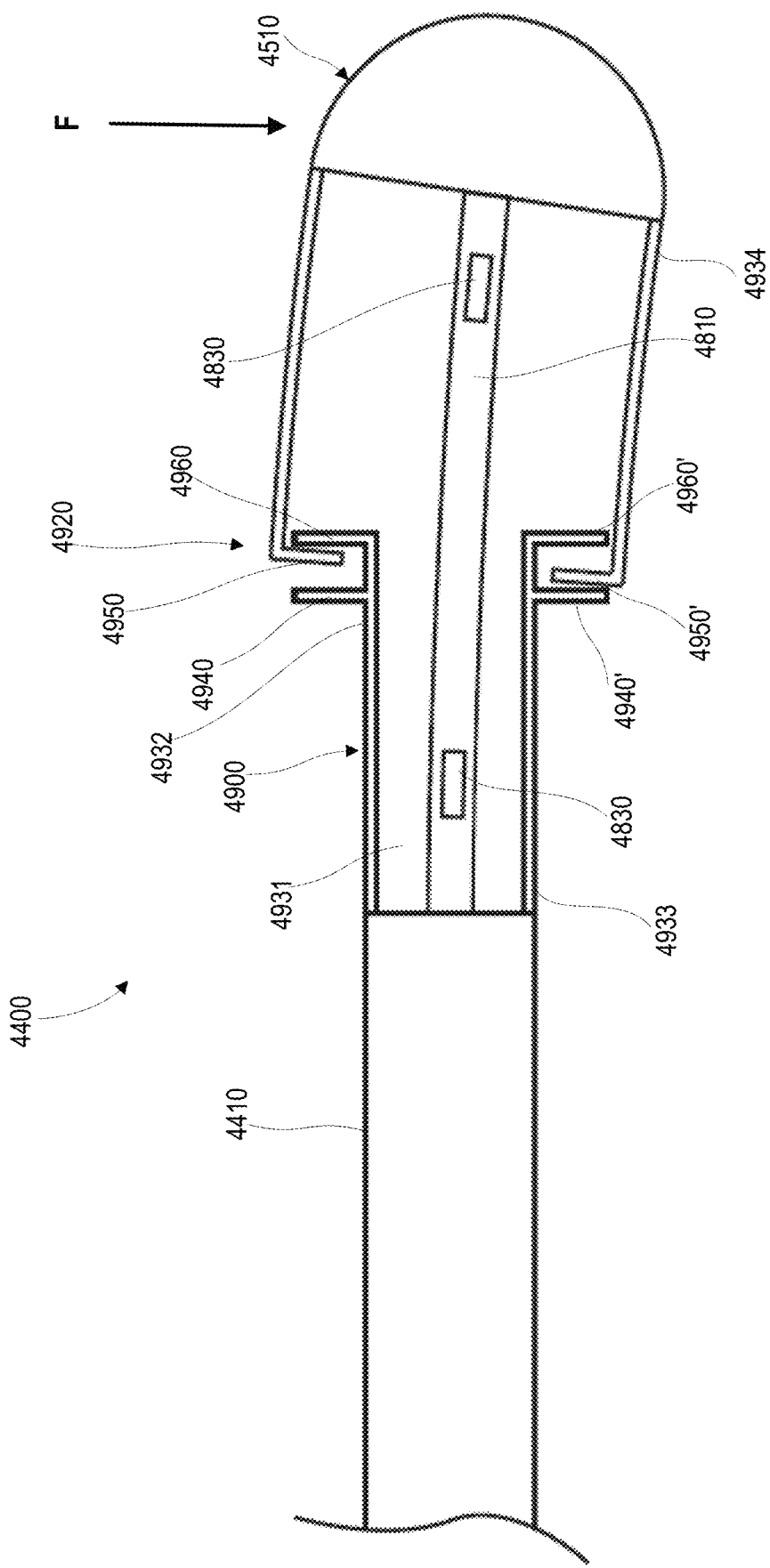
FIG. 10B is a diagrammatic illustration of the portion of the medical device of FIG. 10A shown in a second configuration when a force is exerted on a distal end portion of the medical device.

FIGS. 9A and 9B illustrate an embodiment with interlocking components (including stop surfaces) on only one side of the hard stop structure 3900. In other embodiments, as shown for example in FIGS. 10A and 10B, a hard stop structure includes at least two sets of interlocking components 3920 (which function as stop surfaces) on opposite sides of the hard stop structure. In this manner, the hard stop structure 3900 can produce multiple points of contact when the strain in the beam exceeds a preset amount. FIGS. 10A and 10B are schematic illustrations of a portion of a distal end portion of a medical instrument 4400, according to an embodiment. The surgical instrument 4400 includes a shaft 4410, a hard stop structure 4900, a force sensor unit 4800 including a beam 4810, and strain sensors (e.g., strain gauges) 4830 mounted on a surface along the beam 4810, and a link 4510 coupled at a distal end portion of the surgical instrument 4400. The link 4510 can be, for example, part of or coupled to an end effector (not shown) that can include, for example, articulatable jaws or another suitable surgical tool. In some embodiments, the link 4510 can be included within a wrist assembly having multiple articulating links. A proximal portion of the beam 4810 is coupled to the shaft 4410 and a distal portion of the beam 4810 is coupled to the link 4510. In some embodiments, the distal end portion of the shaft 4410 is coupled to the proximal portion of the beam 4810 via another coupling component (such as an anchor or coupler, not shown). The shaft 4410 can also be coupled at a proximal end portion to a mechanical structure (not shown in FIGS. 10A and 10B) configured to move one or more components of the surgical instrument. The mechanical structure can be similar to the mechanical structure 7700 described in more detail below with reference to medical instrument 7400.

The hard stop structure 4900 includes a proximal end portion 4933, a distal end portion 4934, and a middle portion 4932 between the proximal end portion 4933 and the distal end portion 4934. The hard stop structure 4900 includes a wall that defines an interior region 4931 within which the beam 4800 can be at least partially disposed. In this manner, the wall 4921 has a first side 4922 (shown as the side above the beam 4810) and a second, opposite side 4923 (shown as the side below the beam 4810). In some embodiments, the hard stop structure 4900 can only partially surround the beam 4810. In other embodiments, the hard stop structure 4900 can be cylindrical. As shown in FIGS. 10A and 10B, the hard stop structure 4900 is at least partially open along its length and around at least a portion of its circumference such that the interior lumen 4931 of the hard stop structure 4900 can be viewed. As shown in FIGS. 10A and 10B, the proximal end portion 4933 of the hard stop structure 4900 is coupled to the shaft 4410 and the distal end portion 4934 of the hard stop structure 4900 is coupled to the link 4510. The proximal end portion 4933 can be fixedly coupled to the shaft 4410 and the distal end portion 4934 can be coupled to the link 4510 by any suitable mechanism, such as, for example, by a weld or an adhesive. In this manner, displacement of the link 4510 relative to the shaft 4410 will cause displacement of the distal end portion 4934 of the hard stop structure 4900 relative to the proximal end portion 4933 of the hard stop structure 4900.

The hard stop structure 4900 also includes a first opening 4935 and a second opening 4935' defined by the wall 4921 of the hard stop structure 4900. In this embodiment, the opening 4935 defines interlocking components 4940, 4950 and 4960 on the wall 4921 of the hard stop structure 4900 on the first side 4922 of the hard stop structure 4900 and the opening 4935' defines interlocking components 4940', 4950' and 4960' on the second, opposite side 4923 of the hard stop structure 4900. The openings 4935 and 4935' in the hard stop structure 4900 can each extend at least partially circumferentially around the hard stop structure 4900 such that additional interlocking components can be defined at different locations along the hard stop structure 4900.

As described above for previous embodiments, the hard stop structure 4900 can limit the displacement of the beam 4810 relative to a center axis C-A of the shaft 4410 and/or relative to a center axis $A_B$ of the beam 4810 when a strain in the beam 4810 exceeds a preset amount or when the beam 4810 bends or is displaced a preset amount (e.g., preset bending angle). More specifically, when a force F (shown in FIG. 10B) is imparted on a distal portion of the medical device (e.g., at link 4510) in the X or Y directions (see FIGS. 8A and 8B for reference to X, Y and Z directions), such transverse force can cause the beam 4810 to bend (about either or both of the X axis or the Y axis), which can result in a tensile strain imparted to one side of the beam 4810 and a compression strain imparted to the opposite side of the beam 4810. The strain sensors 4830 on the beam 4810 can measure such tensile and compression strains. As the beam 4810 bends to a preset bending angle, a surface of the component 4950 will contact a surface of the component 4960 and a surface of the component 4950' will contact a surface of the component 4940' on the opposite side of the hard stop structure 4900. In this example, the surfaces of the components 4950 and 4960 and the surfaces of the components 4950' and 4940' function as stop surfaces to prevent the hard stop structure 4900 and the beam 4810, which is coupled to the same components of the medical device as the hard stop structure 4900 (i.e., the link and the shaft) from further displacement or bending. Thus, in this embodiment, the hard stop structure 4900 includes two pairs of stop surfaces that can prevent further bending or displacing of the beam 4810. Specifically, one pair of stop surfaces contacts each other on the side of the hard stop structure 4900 that is under compression and another pair of stop surfaces contacts each other on side of the hard stop structure 4900 that is under tension. Thus, in such an embodiment, the hard stop structure 4900 produces a reactive moment instead of a single reactive force when the hard stop surfaces engage each other.

Figure 11A:
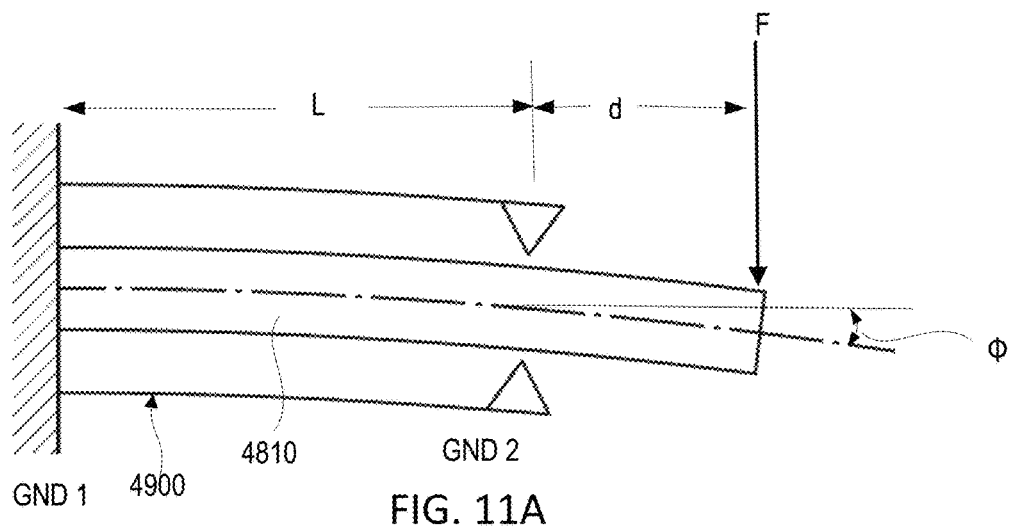
FIGS. 11A and 11B are free-body diagrams of the portion of the medical device shown in FIGS. 10A and 10B in the second configuration.
Figure 11B:
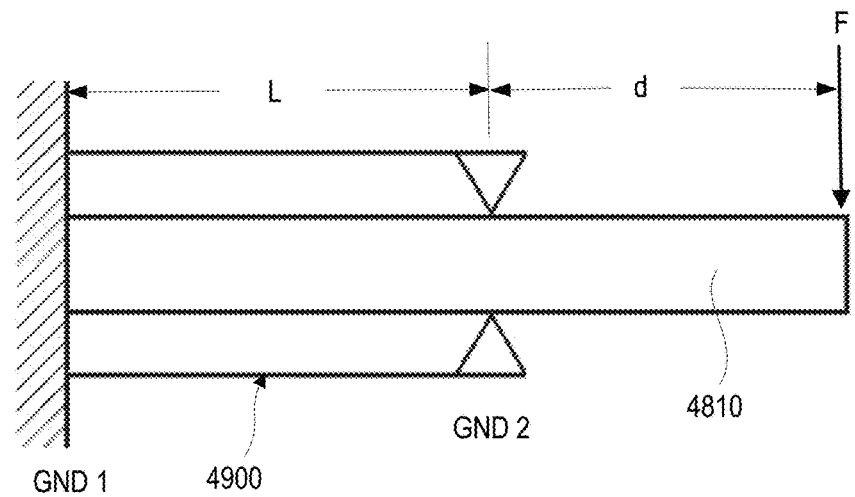

To further illustrate how the multiple points of contact reduce the likelihood of force distortion of the force sensor unit 4800, FIGS. 11A and 11B show free-body diagrams of the medical instrument 4400 of FIGS. 10A and 10B. Specifically, FIG. 11A is a free-body diagram showing the distance L, which is the distance from the base (point GND 1) of the beam 4810 to the point where the hard stop structure 4900 will ultimately contact the beam (point GND 2). The distance d represents the distance between the point where the hard stop structure 4900 will ultimately contact the beam 4810 (point GND 2) and where the force F is applied to the distal tip component. In FIG. 11A the beam 4810 and the hard stop structure 4900 are in a condition where, like shown in FIG. 10A, the hard stop structure does not limit the displacement of the beam. Thus, the beam is free to deflect by a bending angle Φ (FIG. 11A) until the beam reaches a preset bending angle (referred to as ($\Phi_{max}$)). When the bending angle is less than $\Phi_{max}$, the influence of the hard stop structure on the bending of the beam is negligible. The bending of the beam at the point GND 2 can be modeled as set forth in Eqs. (3) and (4):

$$-\Phi = \frac{FL^2}{2EI} - \frac{ML}{EI} \qquad \text{Eq. (3)}$$

$$M = Fd \qquad \text{Eq. (4)}$$

Where E is the modulus of elasticity of the beam and I is the moment of inertia of the XY cross-section of the beam. Substituting Eq. (4) into Eq. (3) yields the following equation for the bending angle, which can be rearranged for the force F applied to the distal tip component:

$$\Phi = \frac{FL^2}{2EI} + \frac{FdL}{EI} \qquad \text{Eq. (5)}$$

$$F = \frac{\Phi EI}{L(L+2d)} \qquad \text{Eq. (6)}$$

Accordingly, when the bending angle has reached the preset maximum bending angle, Eq. (6) can be expressed as:

$$F_{MAX} = \frac{\Phi_{max} EI}{L(L+2d)} \qquad \text{Eq. (7)}$$

FIG. 11B shows the condition where F has exceeded $F_{MAX}$ and the beam 4810 and the hard stop structure 4900 are in a condition where, like shown in FIG. 10B, the surfaces of the components 4950 and 4960 and the surfaces of the components 4950' and 4940' function as stop surfaces to prevent the hard stop structure 4900 and the beam 4810 from further bending. In this condition, the hard stop structure functions as a parallel cantilevered support member with the beam. Although FIG. 11B is a free-body diagram to model the behavior at forces greater than $F_{MAX}$, the beam and the hard stop are shown as being straight for purposes of clarity. At this condition, the force, the bending angle, and the deflection at point GND 2 can be represented as:

$$F = F_{MAX} + \Delta F \qquad \text{Eq. (8)}$$

$$\Phi = \Phi_{max} + \Delta\Phi \qquad \text{Eq. (9)}$$

$$\delta = \delta_{max} + \Delta\delta \qquad \text{Eq. (10)}$$

Figure 11C:
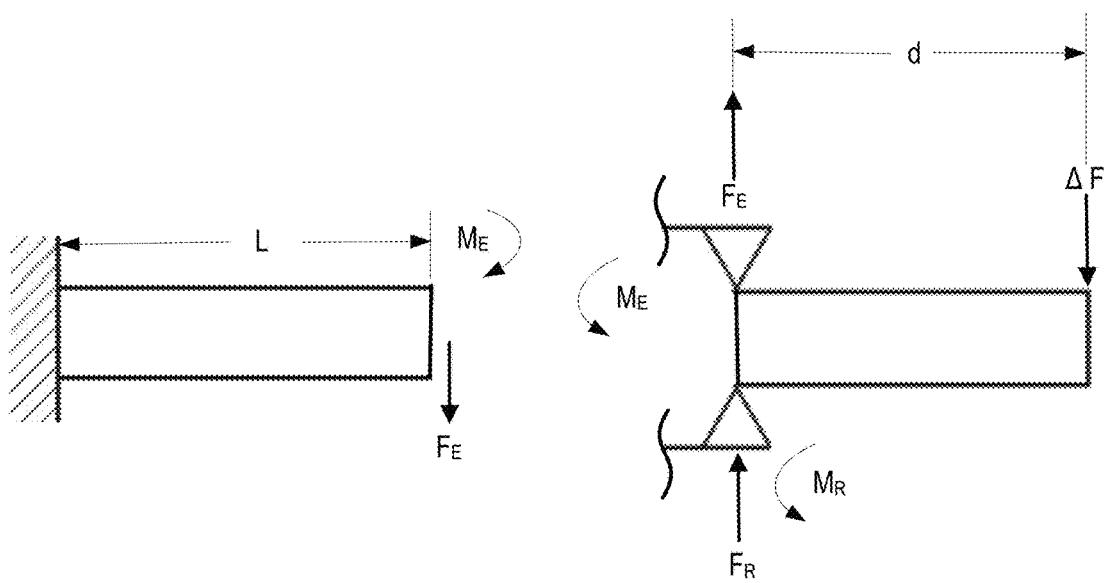
FIG. 11C is a free-body diagram of the portion of the medical device shown in FIGS. 11A and 11B being analyzed at a point of contact.

Because the Eq. (3) through Eq. (7) apply for conditions where the force F is less than or equal to $F_{MAX}$, FIG. 11C is simplified to model the ΔF only, with the beam "cut" at point GND 2. FIG. 11C shows the reactive force $F_R$ produced by the contact of pairs of stop surfaces of the hard stop structure 4900. Importantly, because the hard stop structure has two points of contact (on opposite sides of the beam), the hard stop structure also produces a reactive moment $M_R$ at point GND 2. FIG. 11C also shows the effective force $F_E$ and the effective moment $M_E$ produced by the cantilever coupling to the shaft. Modeling the beam at the point of contact (at GND 2) using the force and moment equations provides:

$$F_E + F_R - \Delta F = 0 \qquad \text{Eq. (11)}$$

$$M_E + M_R - \Delta F d = 0 \qquad \text{Eq. (12)}$$

Because the hard stop structure is rigidly connected to the beam when the pairs of surfaces contact each other, the deflection δ and bend angle Φ of the beam at point GND 2 (length L) is modeled as being the same as that of the hard stop structure. Accordingly, the deflection δ and bend angle Φ are given by:

$$\Delta\Phi = \frac{F_E L^2}{2EI} + \frac{M_E L}{EI} = \frac{F_R L^2}{2E_H I_H} + \frac{M_R L}{E_H I_H} \qquad \text{Eq. (13)}$$

$$\Delta\delta = \frac{F_E L^3}{3EI} + \frac{M_E L^2}{2EI} = \frac{F_R L^3}{3E_H I_H} + \frac{M_R L^2}{2E_H I_H} \qquad \text{Eq. (14)}$$

Figure 12A:
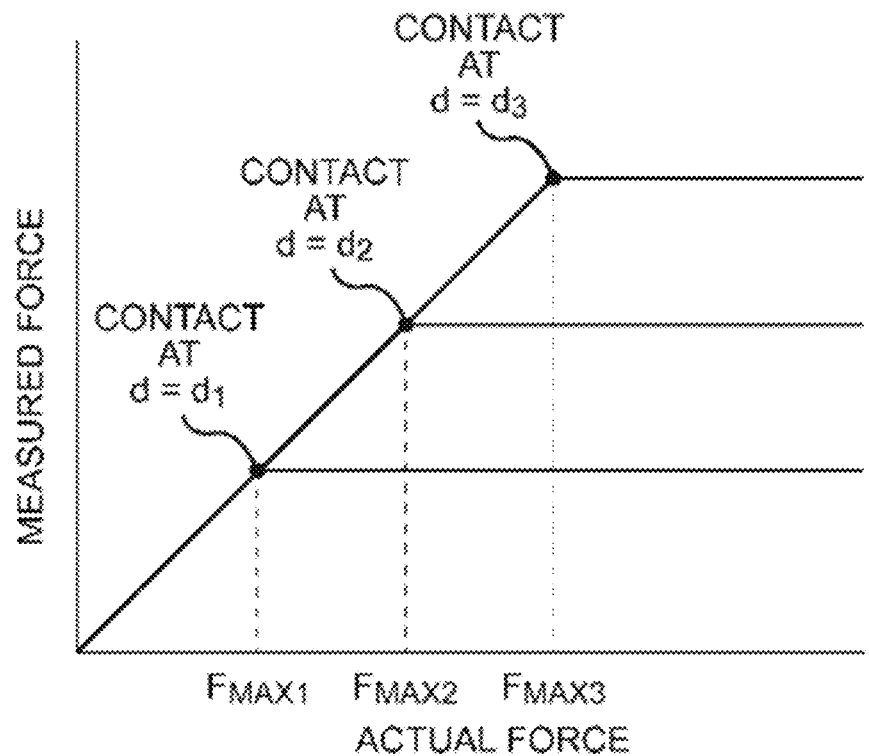
FIGS. 12A and 12B are graphs showing the measured force (Y-axis) as a function of the actual force (X-axis) for the medical device shown in FIGS. 10A and 10B as analyzed according to the free-body diagram of FIG. 11C.

Solving Eq. (11) through Eq. (14) for $F_E$ yields:

$$F_E = \left(\frac{EI}{EI + E_H I_H}\right) \Delta F \qquad \text{Eq. (15)}$$

Where $E_H$ is the modulus of elasticity of the hard stop structure and $I_H$ is the moment of inertia of the XY cross-section of the hard stop structure. The total force of the beam (that will be measured by the strain sensors is given by Eq. (6) when the applied force F is less than $F_{MAX}$. When the applied force F is greater than $F_{MAX}$, however, the total force of the beam is given by:

$$F_{beam} = F_{MAX} + F_E \qquad \text{Eq. (16)}$$

Where $F_E$ is determined by Eq. (15). If the hard stop structure is considered as having an infinite stiffness, then $F_E = 0$. In such situations, after $F_{MAX}$ is reached, the force measured by the strain sensors will remain at $F_{MAX}$ as the actual force applied continues to increase. This condition is shown in FIG. 12A, which is a graph showing measured force (based on the strain signals) as a function of the actual force applied. As shown, when the hard stop structure does not limit the displacement of the beam (i.e., the stop surfaces are not in contact with each other), the beam is free to deflect and the relationship between the measured force and the actual force is linear, which allows for an accurate calibration (i.e., based on the slope of the line). At conditions where the two sets of stop surfaces are in contact (i.e., at the condition where the applied force F is equal to or greater than the $F_{MAX}$), the measured force remains substantially constant (at a value of $F_{MAX}$) as the applied force increases. In this manner, the hard stop structure 4900 prevents the measured force from decreasing, thereby minimizing the problem of force distortion (or inversion).

Figure 12B:
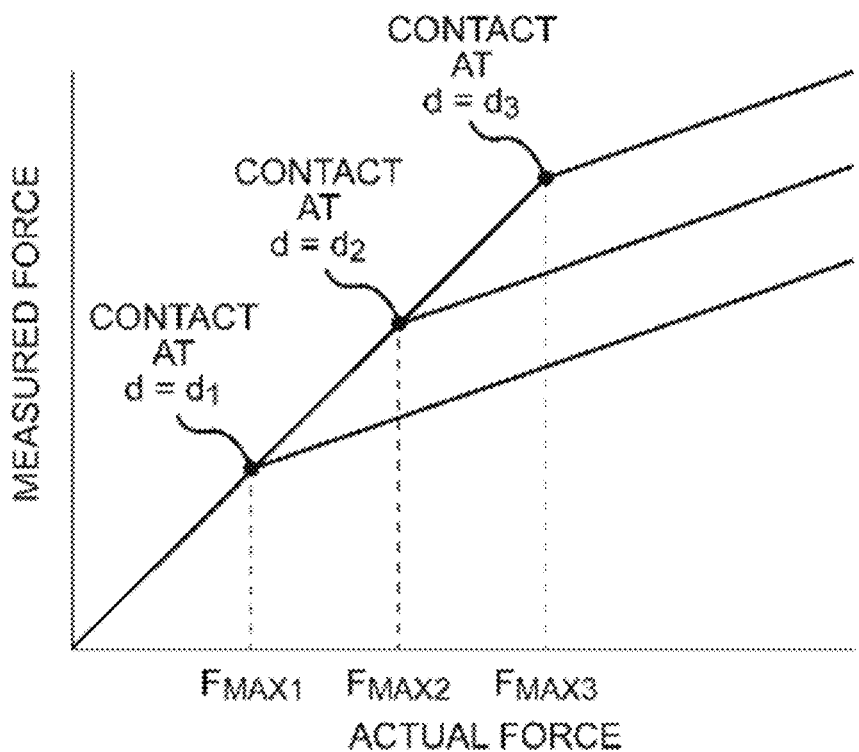

If the hard stop structure is considered as having a finite stiffness, then $F_E$ will be nonzero, but will have a high value. In such situations, after $F_{MAX}$ is reached, the force measured by the strain sensors will increase as the actual force applied continues to increase. This condition is shown in FIG. 12B, which is a graph showing measured force (based on the strain signals) as a function of the actual force applied. As shown, when the hard stop structure does not limit the displacement of the beam (i.e., the stop surfaces are not in contact with each other), the beam is free to deflect and the relationship between the measured force and the actual force is linear, which allows for an accurate calibration (i.e., based on the slope of the line). At conditions where the two sets of stop surfaces are in contact (i.e., at the condition where the applied force F is equal to or greater than the $F_{MAX}$), the measured force continues to increase as the applied force increases, but does so at a much lower slope.

As shown in both FIGS. 12A and 12B, the magnitude of the distance d impacts the $F_{MAX}$ (the force at which the two sets of stop surfaces are in contact). Specifically, for a given geometry and design, the further away from the contact point (GND 2) the force F is applied the sooner the two sets of stop surfaces will contact. Said another way, as the distance d increases, the $F_{MAX}$ decreases. Thus, the hard stop structure 4900 (and any of the hard stop structures described herein) can be optimized for a desired maximum force $F_{MAX}$ by changing the position of the contact surfaces.

FIGS. 13A-20C are various views of a medical instrument 7400, according to an embodiment. In some embodiments, the instrument 7400 or any of the components therein are optionally parts of a surgical system that performs surgical procedures, and which can include a manipulator unit, a series of kinematic linkages, a series of cannulas, or the like. The instrument 7400 (and any of the instruments described herein) can be used in any suitable surgical system, such as the MIRS system 1000 shown and described above. The instrument 7400 includes a mechanical structure 7700, a shaft 7410, a hard stop structure 7900, a force sensor unit 7800 that includes a beam 7810, a wrist assembly 7500, and an end effector 7460. Although not shown, the instrument 7400 can also include a number of cables that couple the mechanical structure 7700 to the wrist assembly 7500 and end effector 7460. The instrument 7400 is configured such that select movements of the cables produces rotation of the wrist assembly 7500 (i.e., pitch rotation) about a first axis of rotation $A_1$ (see FIG. 13B) (which functions as a pitch axis, the term pitch is arbitrary), yaw rotation of the end effector 7460 about a second axis of rotation $A_2$ (see FIG. 13B) (which functions as the yaw axis, the term yaw is arbitrary), a cutting rotation of the tool members of the end effector 7460 about the second axis of rotation $A_2$, or any combination of these movements. Changing the pitch or yaw of the instrument 7400 can be performed by manipulating the cables in a similar manner as described, for example, in U.S. Pat. No. 8,821,480 B2 (filed Jul. 16, 2008), entitled "Four-Cable Wrist with Solid Surface Cable Channels,", which is incorporated herein by reference in its entirety. Thus, the specific movement of each of the cables to accomplish the desired motion is not described below.

The shaft 7410 includes a proximal end (not shown) that is coupled to the mechanical structure 7700, and a distal end 7412 (see FIGS. 13C and 14B) that is coupled to the beam 7810 via an anchor 7925. In some embodiments, the proximal end of the shaft 7410 is coupled to the mechanical structure 7700 in a manner that allows movement of the shaft 7410 along a center axis C-A of the shaft 7410 (shown in FIG. 13C) relative to the mechanical structure 7700. Allowing the shaft 7410 to "float" in the Z direction facilitates measurement of forces along the Z axis, as described herein. In some embodiments, the proximal end of the shaft 7410 can be movably coupled to the mechanical structure 7700 via a four bar linkage of the types shown and described in International Patent Appl. No. PCT/US2019/061883 (filed Nov. 15, 2019), entitled "Surgical Instrument with Sensor Aligned Cable Guide," which is incorporated herein by reference in its entirety. The shaft 7410 also defines a lumen (not shown) and/or multiple passageways through which the cables and other components (e.g., electrical wires, ground wires, or the like) can be routed from the mechanical structure 7700 to the wrist assembly 7500. The anchor 7925 can be received at least partially within the lumen of the shaft 7410 and can be fixedly coupled to the shaft 7410 via an adhesive bond, a weld, or any other permanent coupling mechanism (i.e., a coupling mechanism that is not intended to be removed during normal use).

The mechanical structure 7700 produces movement of the cables (not shown) to produce the desired movement (pitch, yaw, or grip) at the wrist assembly 7500. Specifically, the mechanical structure 7700 includes components and controls to move some of the cables in a proximal direction (i.e., to pull in certain cables) while simultaneously allowing the distal movement (i.e., releasing or "paying out") of other of the cables in equal lengths. In this manner, the mechanical structure 7700 can maintain the desired tension within the cables, and in some embodiments, can ensure that the lengths of the cables are conserved (i.e., moved in equal amounts) during the entire range of motion of the wrist assembly 7500. In other embodiments, however, conservation of the lengths of the cables is not required.

In some embodiments, the mechanical structure 7700 can include one or more mechanisms that produce translation (linear motion) of a portion of the cables. Such a mechanisms can include, for example, a gimbal, a lever, or any other suitable mechanism to directly pull (or release) an end portion of any of the cables. For example, in some embodiments, the mechanical structure 7700 can include any of the mechanical structures (referred to as backend assemblies or actuators) or components described in U.S. Patent Application Pub. No. US 20157/0047454 A1 (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety. In other embodiments, however, the mechanical structure 7700 can include a capstan or other motor-driven roller that rotates or "winds" a portion of any of the bands to produce the desired band movement. For example, in some embodiments, the mechanical structure 7700 can include any of the mechanical structures (referred to as backend assemblies or actuators) or components described in U.S. Pat. No. 9,204,923 B2 (filed Jul. 16, 2008), entitled "Medical Instrument Electronically Energized Using Drive Cables," which is incorporated herein by reference in its entirety.

Figure 13A:
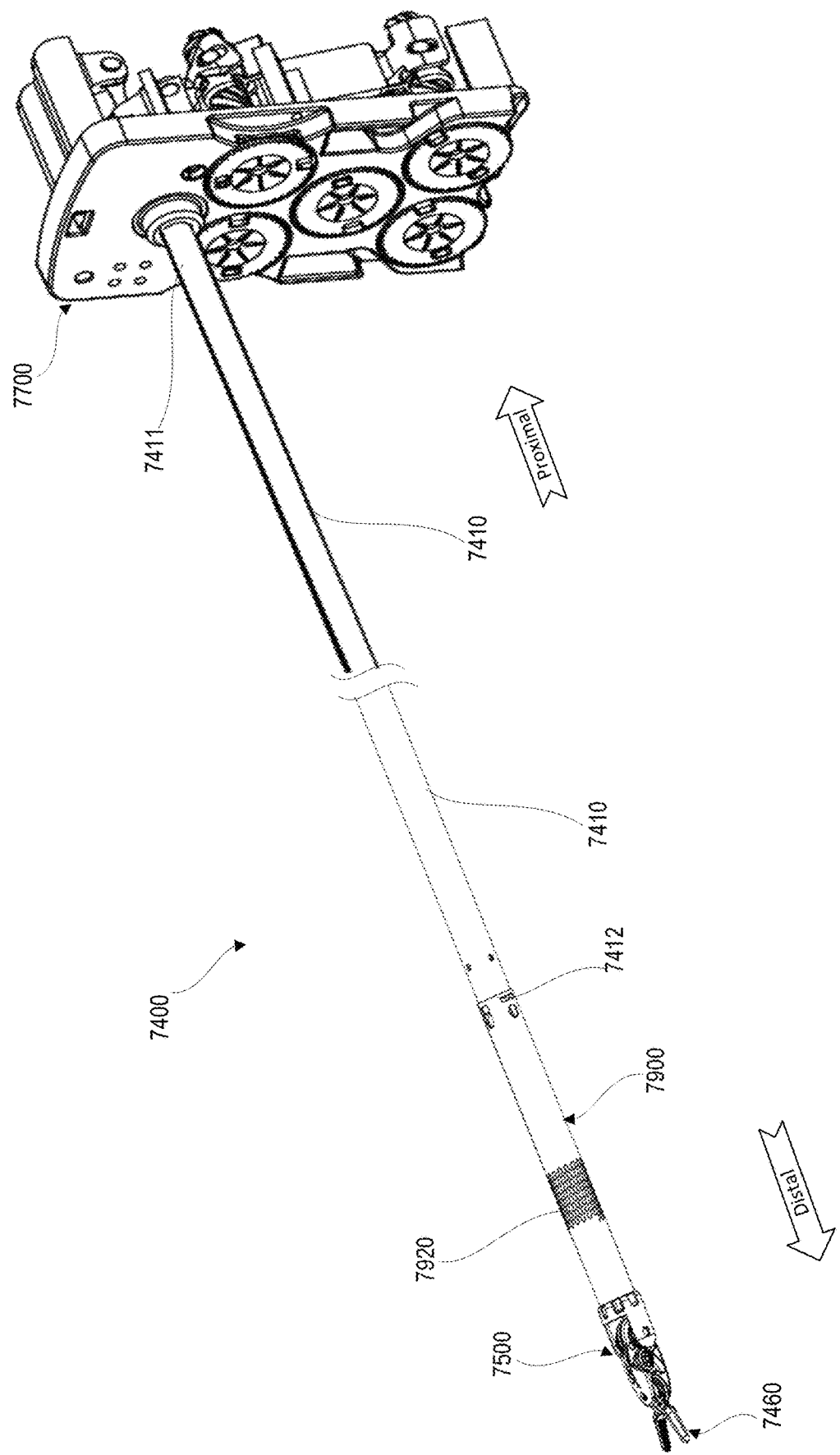
FIG. 13A is a perspective view of a medical device according to an embodiment.
Figure 13B:
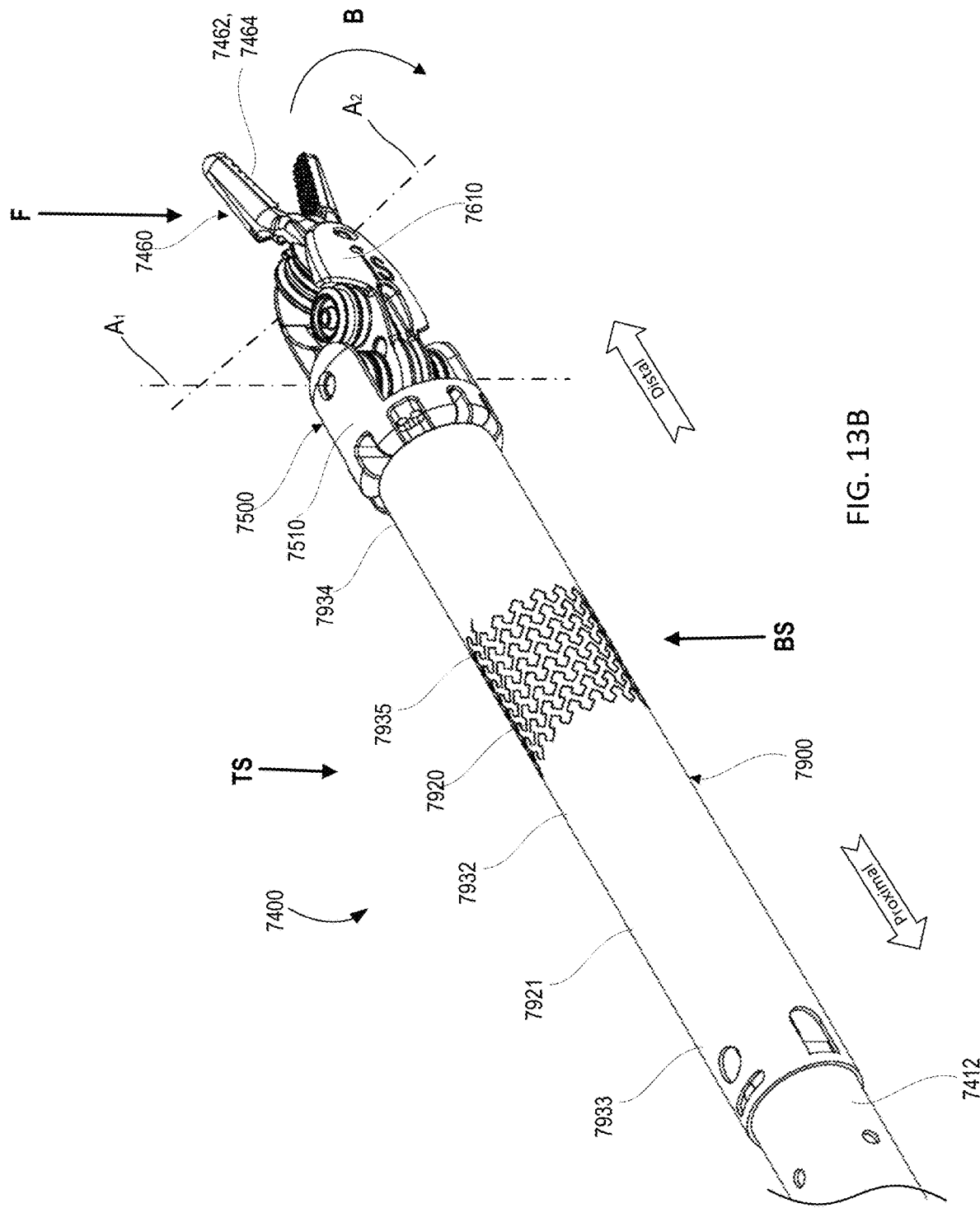
FIG. 13B is an enlarged perspective view of a distal end portion of the medical device of FIG. 13A.
Figure 13C:
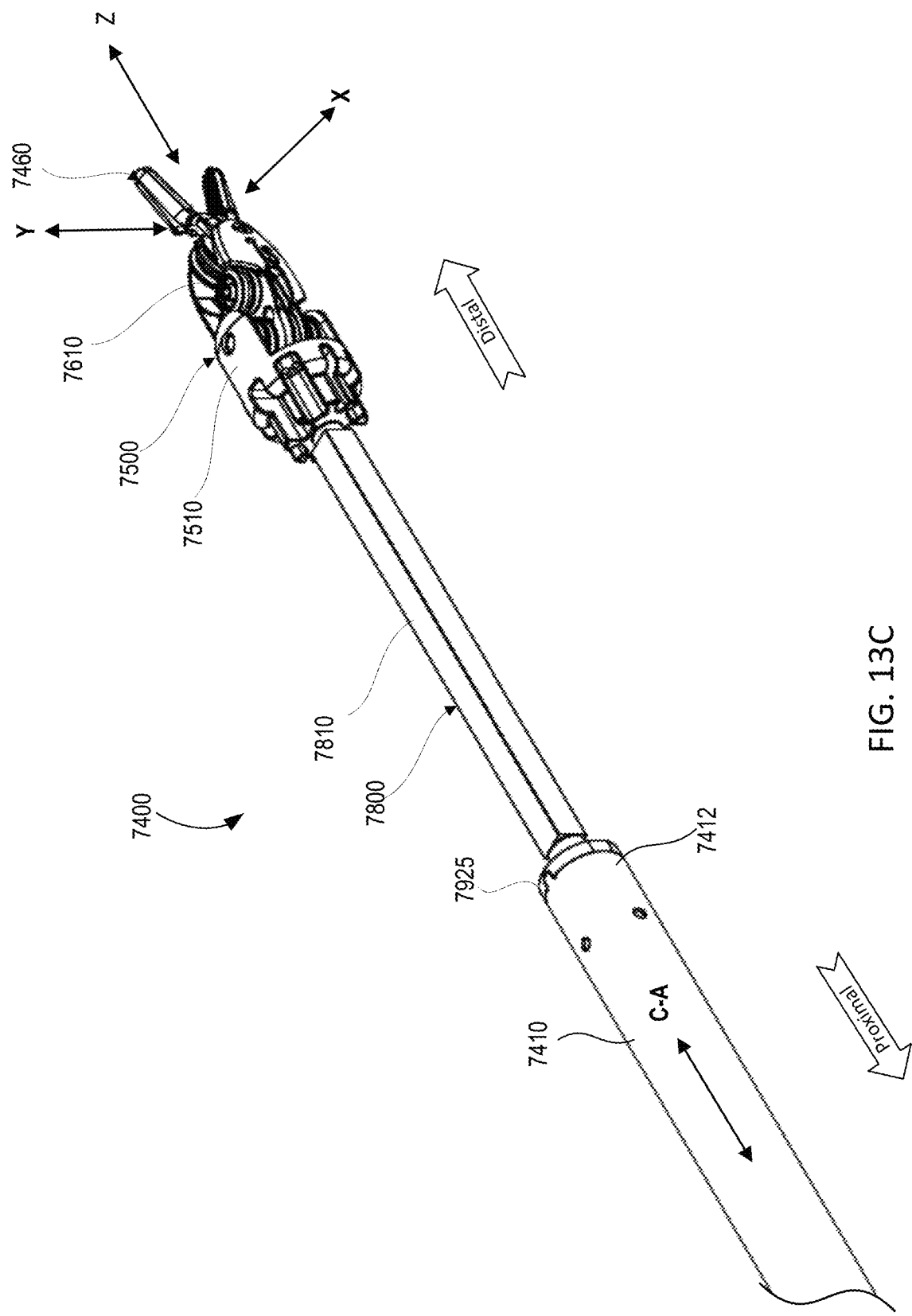
FIG. 13C is an enlarged perspective view of a distal end portion of the medical device of FIG. 13A.
Figure 14A:
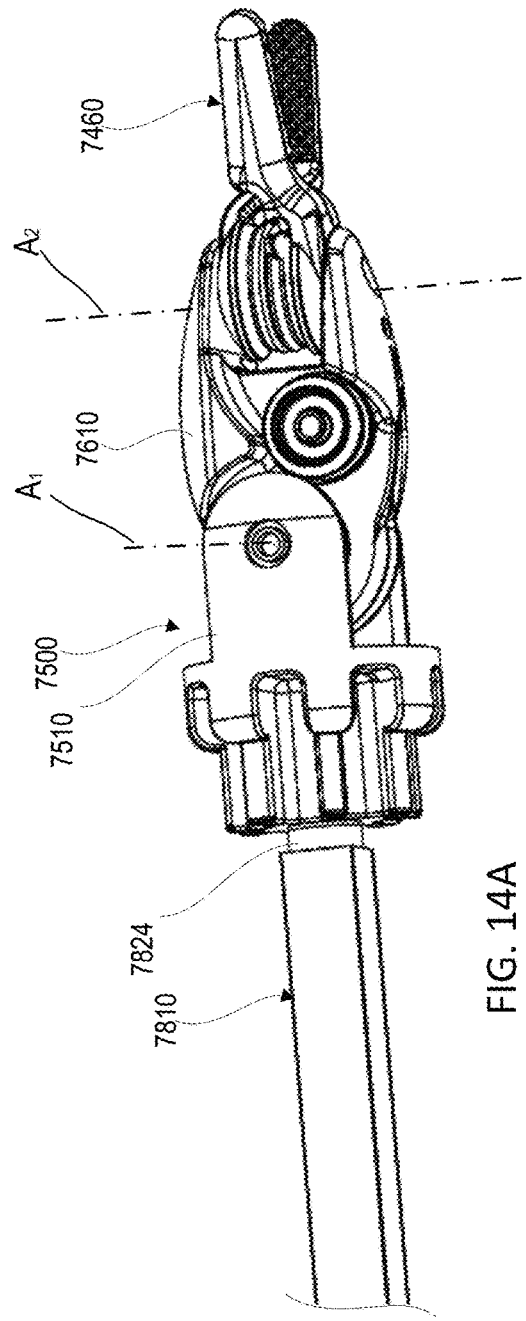
FIG. 14A is a perspective view of a distal portion of the medical device of FIG. 13A.
Figure 14B:
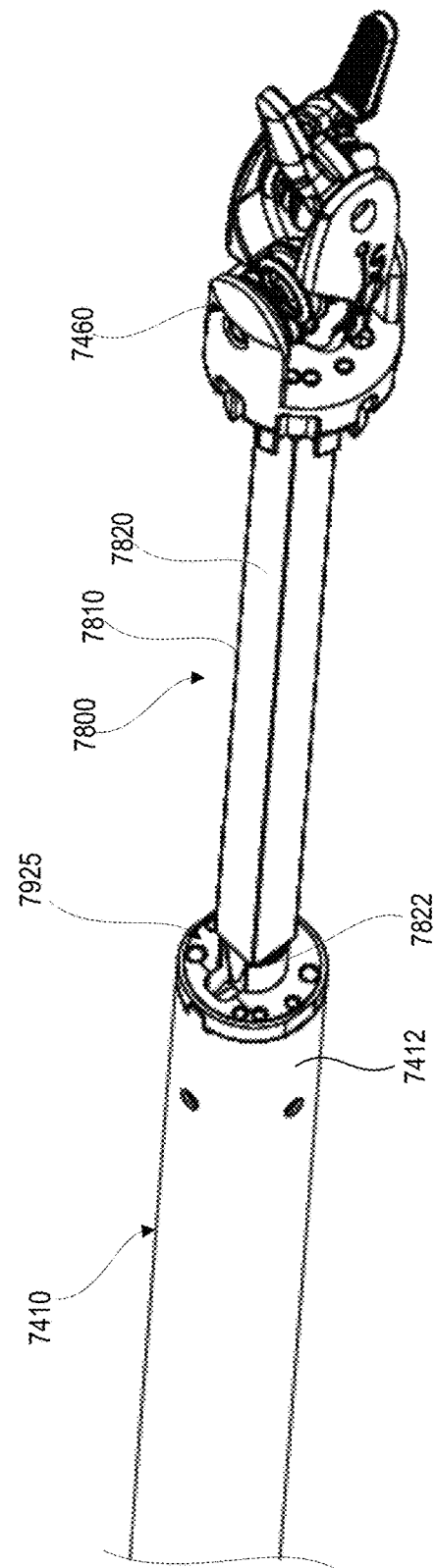
FIG. 14B is a perspective distal end view of the shaft and anchor of the medical device of FIG. 13A.
Figure 15:
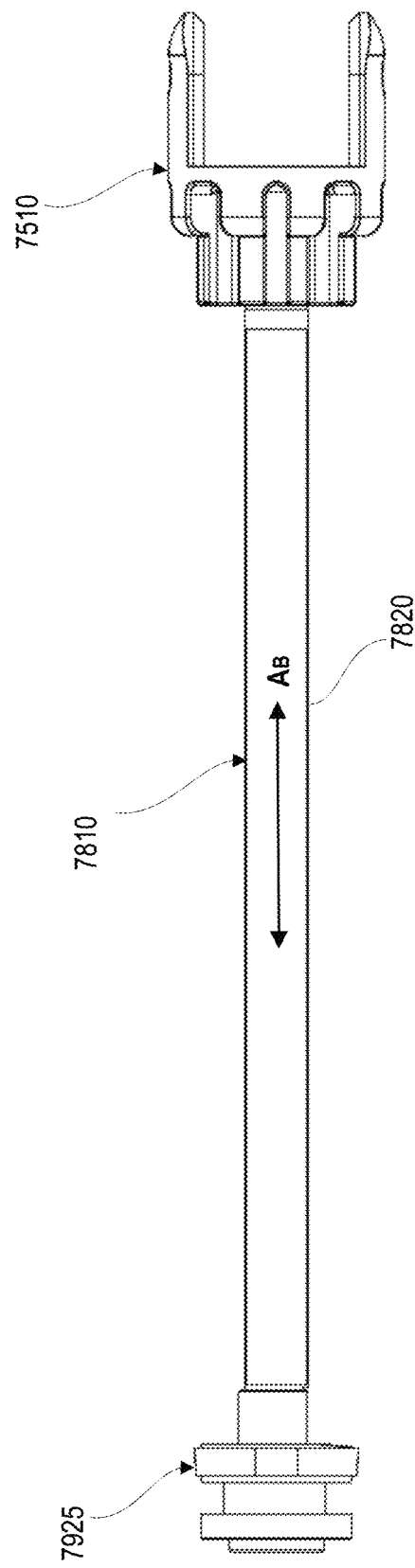
FIG. 15 is a side view of the beam, distal link and anchor of the medical device of FIG. 13A.
Figure 16:
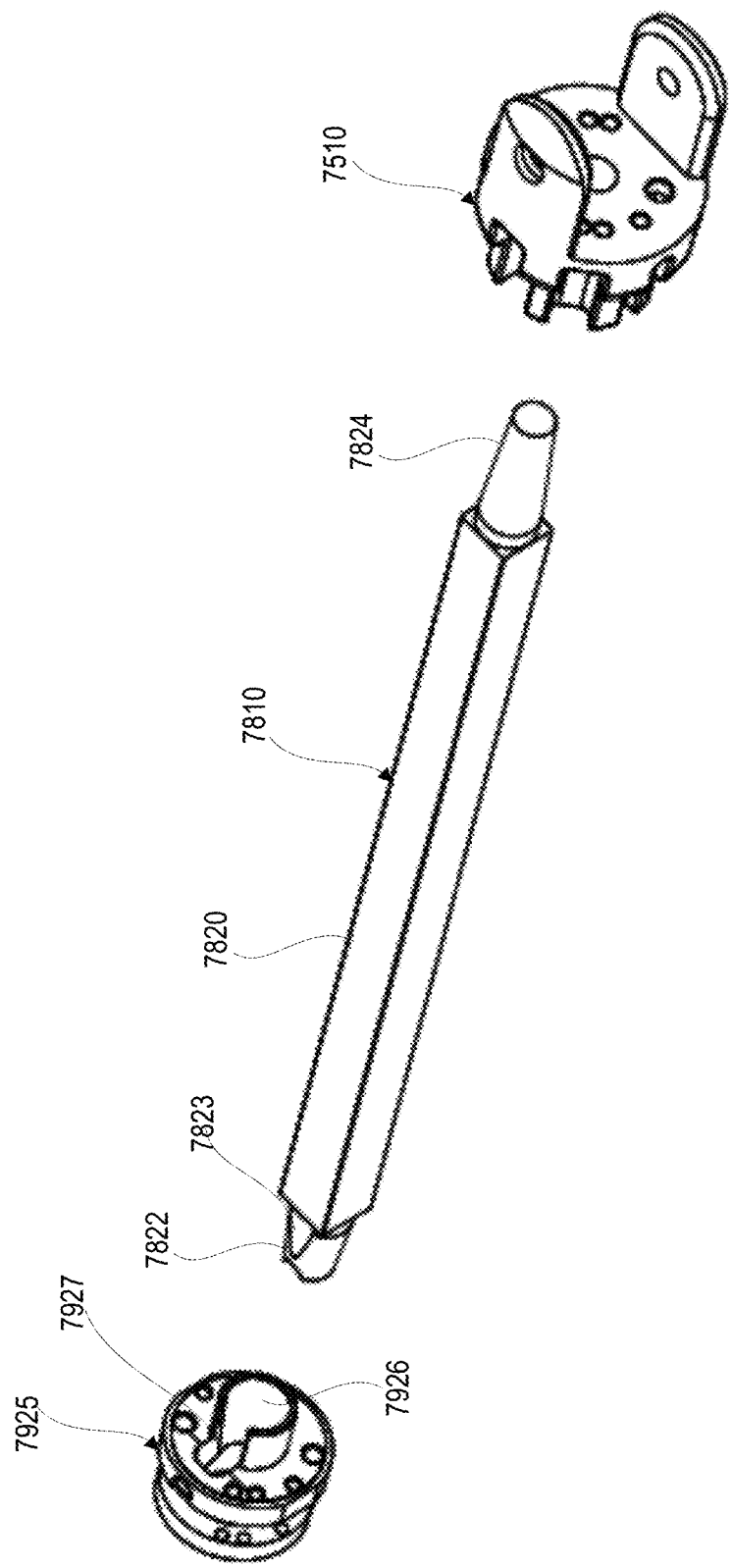
FIGS. 16 and 17 are each an exploded view of the beam, distal link and anchor of FIG. 15 showing a distal perspective (FIG. 16) and a proximal perspective (FIG. 17).
Figure 17:
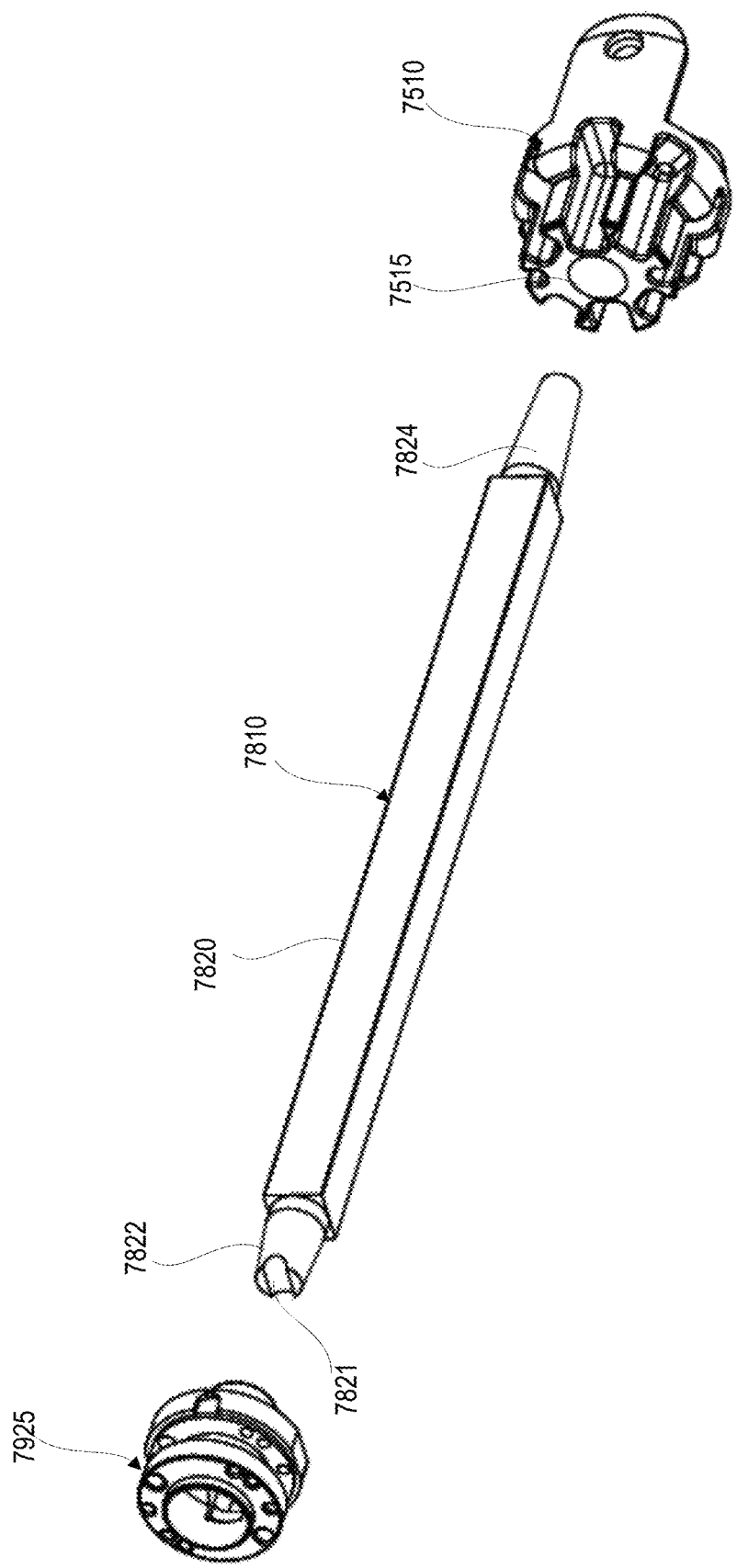
Figure 18:
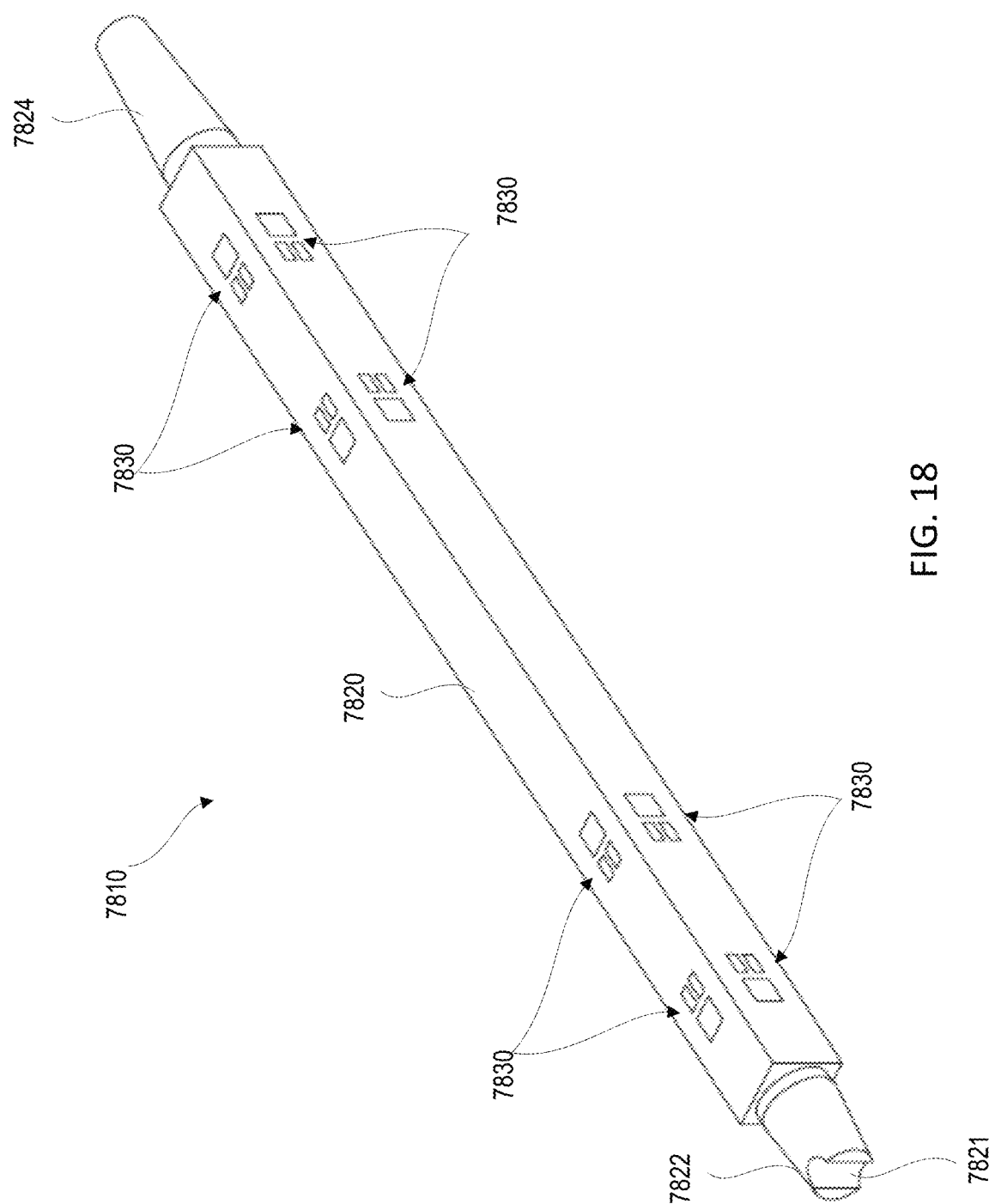
FIG. 18 is a perspective view of the beam of the medical device of FIG. 13A illustrating strain sensors mounted thereto.

Referring to FIG. 13B, the wrist assembly 7500 includes a proximal first link 7510 and a distal second link 7610. The first link 7510 includes a distal portion that is coupled to a proximal portion of the second ink 7610 at a joint such that the second link 7610 can rotate relative to the first link 7510 about a first axis of rotation $A_1$ (which functions as the pitch axis, the term pitch is arbitrary). The proximal first link 7510 includes a proximal portion that is coupled to the beam 7810 as described in more detail below.

A distal end of the distal second link 7610 is coupled to the end effector 7460 such that the end effector 7460 can rotate about a second axis of rotation $A_2$ (see FIG. 13B) (which functions as the yaw axis). The end effector 7460 can include at least one tool member 7462 having a contact portion 7464 configured to engage or manipulate a target tissue during a surgical procedure. For example, in some embodiments, the contact portion 7464 can include an engagement surface that functions as a gripper, cutter, tissue manipulator, or the like. In other embodiments, the contact portion 7464 can be an energized tool member that is used for cauterization or electrosurgical procedures. The end effector 7460 is operatively coupled to the mechanical structure 7700 such that the tool member 7462 rotates relative to shaft 7410 about the first axis of rotation $A_1$. In this manner, the contact portion 7464 of the tool member 7462 can be actuated to engage or manipulate a target tissue during a surgical procedure. The tool member 7462 (or any of the tool members described herein) can be any suitable medical tool member. Moreover, although only one tool member 7462 is identified, as shown, the instrument 7400 can include two tool members that cooperatively perform gripping or shearing functions. In other embodiments, an end effector can include more than two tool members.

The beam 7810 includes a proximal end portion 7822, a middle portion (which functions as an active portion of the beam 7810) and a distal end portion 7824. The beam 7810 has a center axis $A_B$ defined along a length of the beam 7810 (see FIG. 15). One or more strain sensors 7830 (see FIG. 18) are mounted on the middle portion 7820 of the beam 7810. The strain sensors 7830 are not shown in some of the figures for illustrative purposes only. The strain sensors 7830 can be, for example, strain gauges, and can be used to measure forces imparted on the surgical instrument during a surgical procedure as described in more detail below. In this embodiment, the middle portion 7820 defines four side surfaces disposed perpendicular to each other and on which the strain sensors 7830 can be mounted (see FIG. 18). In this embodiment, the cross-section of the middle portion 7820 is substantially square shaped. Thus, the cross-sectional shape of the middle portion 7820 is identical for every ninety degrees of rotation. In this manner, the output from the strain sensors 7830 (which are shown disposed on only two of the four sides of the middle portion 7820) will be consistent throughout the entire range of the roll of the shaft 7410 (i.e., rotation of the shaft 7410 about the center axis $A_B$). In some alternative embodiments, the strain sensors 7830 can be disposed on only a single side of the beam 7810.

Both the distal end portion 7824 and the proximal end portion 7822 of the beam 7810 are tapered but each has a different cross-sectional shape and size than the other. In this embodiment, the proximal end portion 7822 defines an end cutout region 7821 (see FIGS. 17 and 13) that is used for manufacturing purposes and also provides clearance for routing of electrical components (not shown) disposed within the shaft 7410 and anchor 7925. The proximal end portion 7822 also defines a side cutout region 7823 (see FIG. 16) that provides an entry into the lumen of the shaft 7410 (via the cutout 7927 in the anchor) to allow routing of the electrical wiring to the strain sensors 7830.

The beam 7810 is coupled to a distal end portion 7412 of the shaft 7410 via the anchor 7925 and to the proximal link 7510 of the wrist assembly 7500 (see, e.g., FIGS. 13C-15). More specifically, the anchor 7925 defines an opening 7926 (see FIG. 16) that can matingly receive the tapered proximal end portion 7822 of the beam 7810. The anchor 7925 also defines the cutout 7927 through which wires can be routed. The proximal end portion 7822 can be coupled to the anchor 7925 with, for example, welding, an adhesive or other suitable coupling methods. Similarly, the proximal link 7510 defines an opening 7515 (see FIG. 17) that can matingly receive the distal end portion 7824 of the beam 7810. The distal end portion 7824 can be coupled to the link 7510 with, for example, welding, an adhesive or other suitable coupling methods.

Figure 19A:
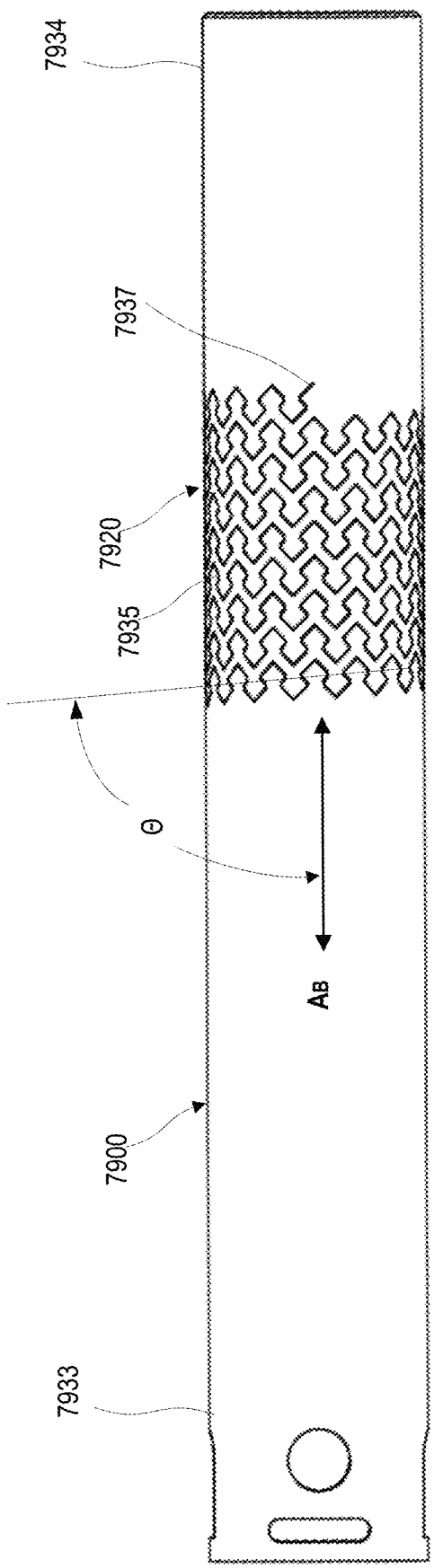
FIGS. 19A and 19B are opposite side views of the hard stop structure of the medical device of FIG. 13A.
Figure 19B:
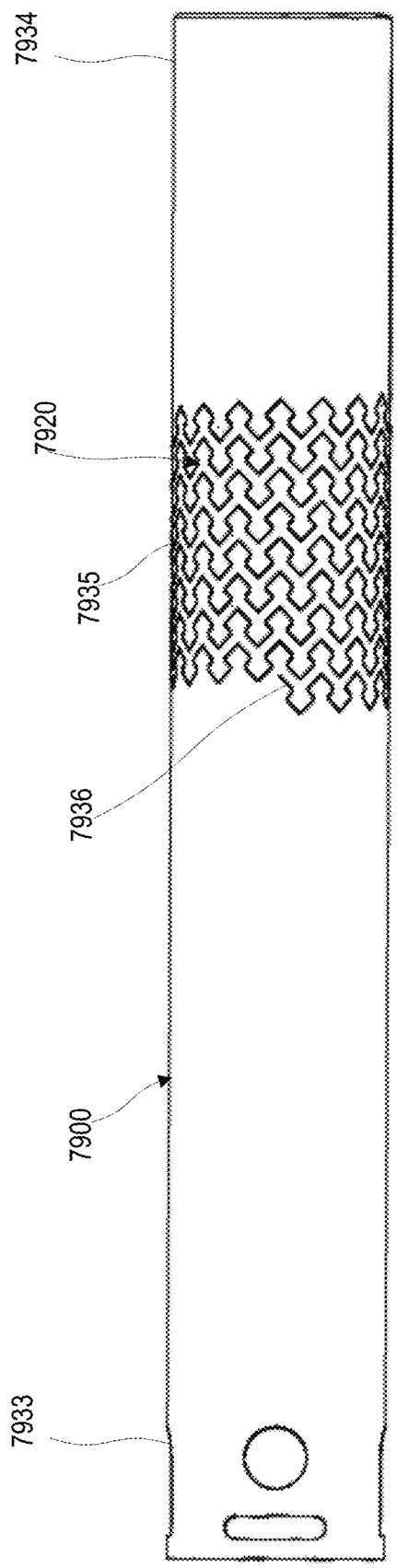

The hard stop structure 7900 includes a proximal end portion 7933, a distal end portion 7934, and a middle portion 7932 between the proximal end portion 7933 and the distal end portion 7934. The hard stop structure 7900 defines an interior lumen (not shown) within which the beam 7810 is disposed. In this embodiment, the hard stop structure 7900 is cylindrical. As shown in FIG. 13B, the proximal end portion 7933 of the hard stop structure 7900 is coupled to the shaft 7410 and the distal end portion 7934 of the hard stop structure 7900 is coupled to the proximal link 7510. The proximal end portion 7933 can be fixedly coupled to the distal end portion 7412 of the shaft 7410 and the distal end portion 4934 can be coupled to the proximal link 7510 by any suitable mechanism, such as, for example, by a weld or an adhesive. As shown in FIGS. 19A and 19B, the proximal end portion 7933 an include a tapered portion and an elongate slot to facilitate fixation to the shaft 7410. In this manner, displacement of the proximal link 7510 relative to the shaft 7410 will cause displacement of the distal end portion 7934 of the hard stop structure 7900 relative to the proximal end portion 7933 of the hard stop structure 7900.

The hard stop structure 7900 also includes an opening 7935 defined by a wall 7921 of the hard stop structure 7900. The opening 7935 can be cut into the wall 7921 of the hard stop structure 7900 by any suitable methods, such as, for example, laser cut, electronic discharge machining, or the like. In some embodiments, the hard stop structure can be a laser-cut tube. In this embodiment, the opening 7935 defines multiple interlocking components that wrap about a circumference of the hard stop structure in a spiral pattern. More specifically, the opening 7935 has a first end point 7936 (see, for example, FIG. 19B), wraps around the circumference of the hard stop structure 7900, and has a second end point 7937 (see, for example, FIG. 19A) on an opposite side of the hard stop structure 7900. The multiple interlocking components 7920 form a repeating pattern within the wall 7921 of the hard stop structure 7900 about the circumference of the hard stop structure 7900. In this manner, the hard stop structure 7900 can limit the range of motion (i.e., bending) of the hard stop structure 7900 and the beam 7810 in all directions lateral to the Z axis, and not just only in the X direction or Y direction.

Figure 20A:
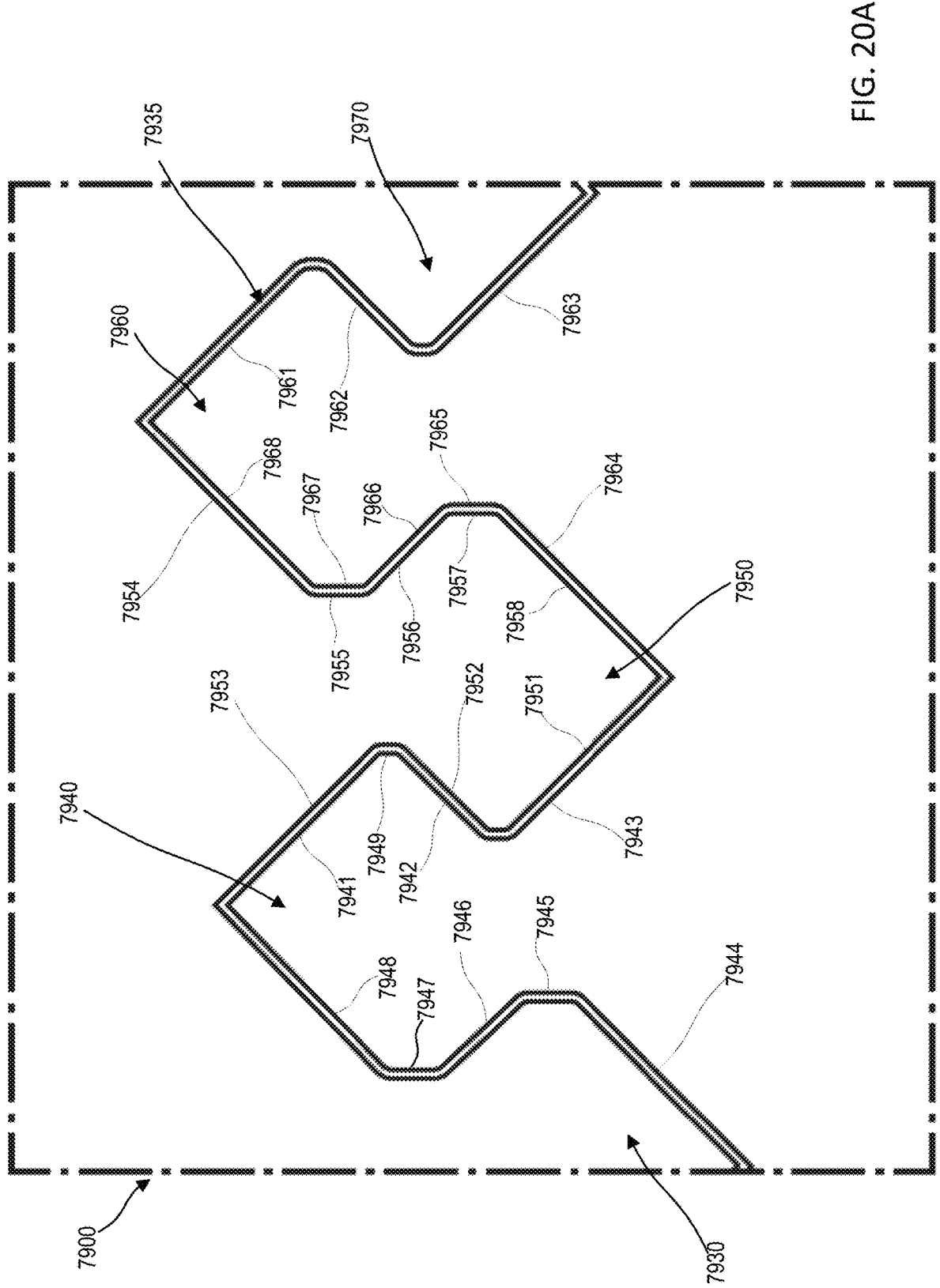
FIG. 20A is an enlarged side view of a portion of the hard stop structure of the medical device of FIG. 13A.
Figure 20B:
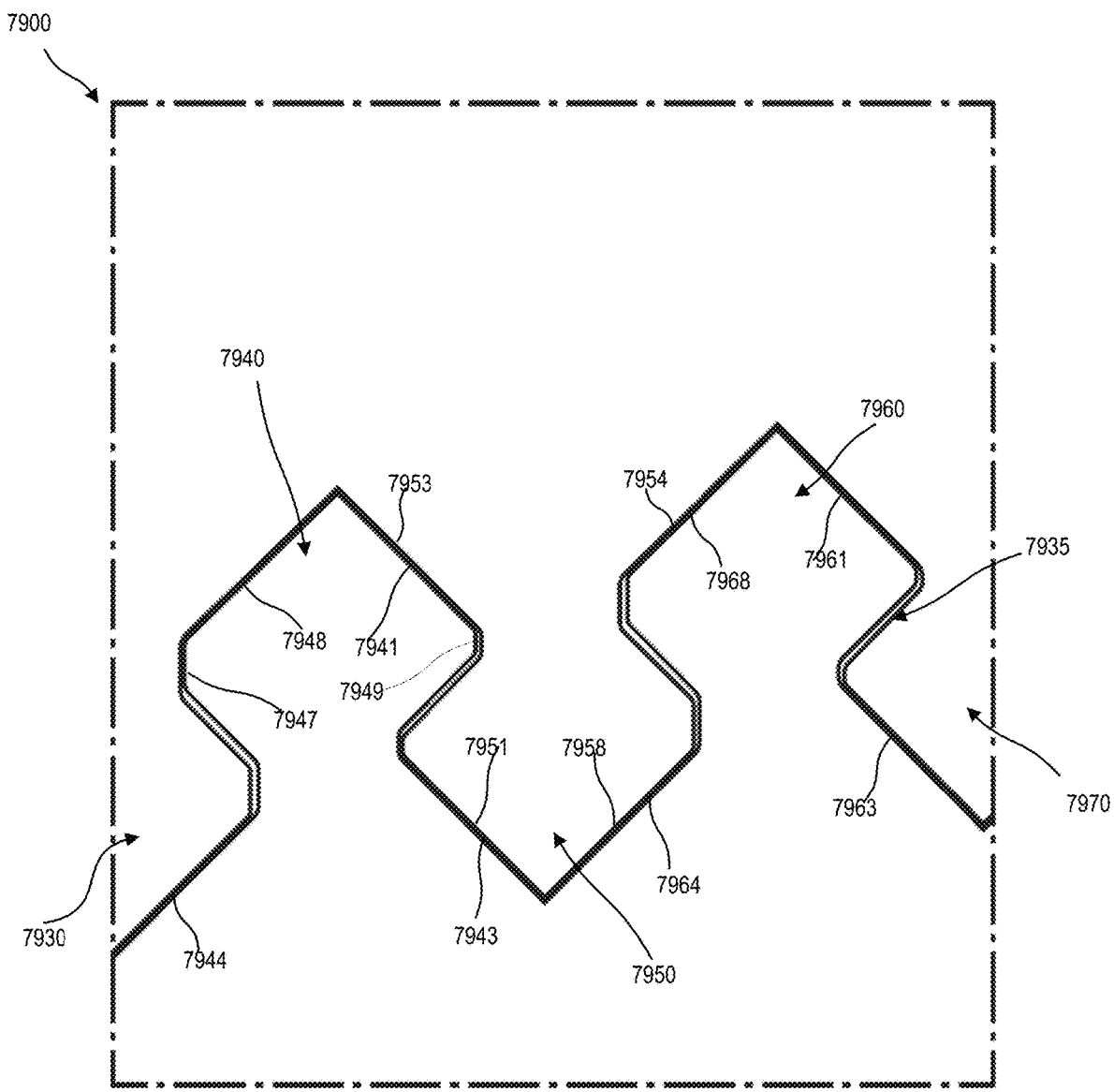
FIGS. 20B and 20C are enlarged side views of a portion of the hard stop structure of the medical device of FIG. 13A showing the hard stop structure in a first configuration when under compression (FIG. 20B) and a second configuration when under tension (FIG. 20C).
Figure 20C:
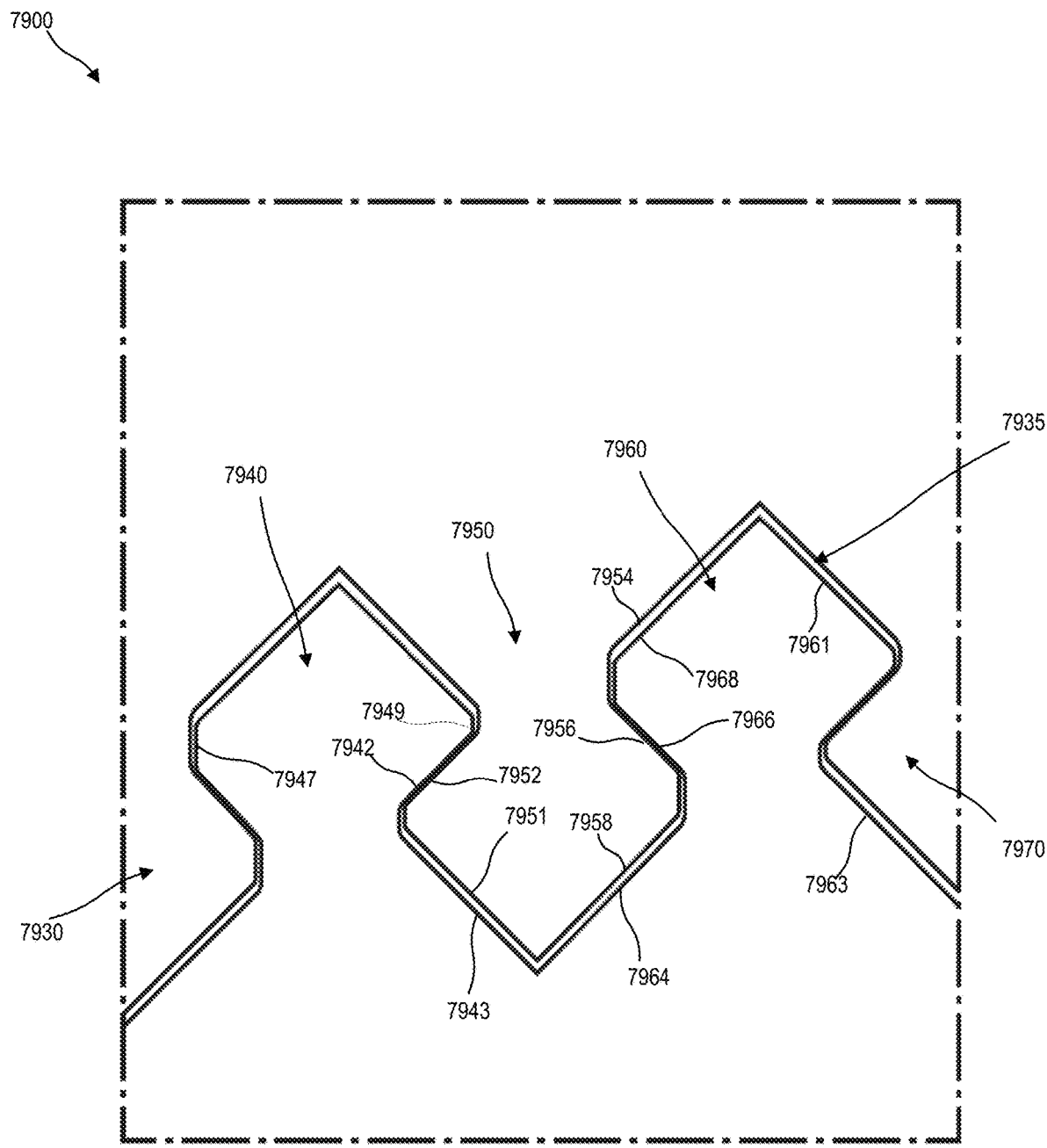

Each of the interlocking components 7920 includes multiple surfaces. As shown in FIGS. 20A-20C, the interlocking components include components 7930 (only partially shown in the enlarged view of FIGS. 20A-20C), 7940, 7950, 7960 and 7970 (only partially shown in the enlarged view of FIGS. 20A-20C). Each of the components include multiple surfaces that contact corresponding surfaces of adjacent components in certain instances when a motion limit has been reached. For example, as shown in FIG. 20A, the component 7940 includes surfaces 7941, 7942, 7943, 7944, 7945, 7946, 7947, and 7948. The component 7950 includes surfaces 7951, 7952, 7953, 7954, 7955, 7956, 7957, 7958 and the component 7960 includes surfaces 7961, 7962, 7963, 7964, 7965, 7966, 7967 and 7968. Components 7930 and 7970 have similar surfaces but are not labeled in FIGS. 20A-20C. More details regarding the function of the hard stop structure 7900 are described below.

In use, the end effector 7460 contacts anatomical tissue, which may result in X, Y, or Z direction forces (see FIG. 13B) being imparted on the end effector 7460 and that may also result in moment forces about the various axes. The strain sensors 7830 (see FIG. 18) can be used to measure strain in the beam as a result of such forces imparted on the end effector 7460. More specifically, the strain sensors 7830 can measure forces imparted on the end effector 7460 that are transverse (e.g., perpendicular) to the center axis $A_B$ of the beam 7810 as such forces are transferred to the beam 7810 in the X and Y directions (see FIG. 13C). Specifically, the transverse forces acting upon the end effector 7460 can cause a slight bending of the beam 7810, which can result in a tensile strain imparted to one side of the beam 7810 and a compression strain imparted to the opposite side of the beam 7810. The strain sensors 7830 are coupled to the beam 7810 to measure such tensile and compression forces.

As described above for previous embodiments, the hard stop structure 7900 can limit the displacement of the beam 7810 relative to a center axis C-A of the shaft 7410 and/or relative to the center axis $A_B$ of the beam 7810 when a strain in the beam 7810 exceeds a preset amount or when the beam 7810 bends or is displaced a preset amount (e.g., preset bending angle). More specifically, when a force F (see FIG. 13B) is imparted on a distal portion of the medical device 7400 (e.g., at end effector 7460) in the X or Y directions (see FIG. 13C for reference to X, Y and Z directions), such transverse force can cause bending the beam 7810 to bend (about either or some combination of the X axis or the Y axis), which can result in a tensile strain imparted to one side of the beam 7810 and a compression strain imparted to the opposite side of the beam 7810. The strain sensors 7830 on the beam 7810 can measure such tensile and compression strains. For example, in this example embodiment, with the force F shown in FIG. 13B, the hard stop structure 7900 and beam 7810 would bend downward in the direction of arrow B such that a tensile strain would be imparted on a top side TS of the beam 7810 and a compression strain would be imparted on a bottom side BS of the beam 7810.

As the beam 7810 bends, specific surfaces of the interlocking components 7920 are configured to engage each other when the beam 7810 bends to a desired preset bending angle or is otherwise displaced to a preset amount. Thus, the surfaces of the interlocking components 7920 function as stop surfaces to prevent the hard stop structure 7900 and beam 7810 from bending (or being displaced any further). More specifically, FIG. 20B is an enlarged view of a portion of the hard stop structure 7900 illustrating the function of the hard stop structure 7900 when compression strain is imparted on a portion of the hard stop structure 7900 and FIG. 20C is an enlarged view of the portion of the hard stop structure illustrating the function of the hard stop structure 7900 when a tensile strain is imparted on the portion of the hard stop structure 7900. As shown in FIG. 20B, when under compression, the surface 7941 of component 7940 contacts the surface 7953 of component 7950, the surface 7954 of component 7950 contacts the surface 7968 of components 7960, the surface 7951 contacts the surface 7943 of component 7940, and the surface 7958 of component 7950 contacts the surface 7964 of component 7960. The same corresponding surfaces of the other adjacent components (e.g., 7930 and 7970) can contact each other in the same manner. For example, the surface 7944 of component 7940 can contact a corresponding surface of component 7930 as shown in FIG. 20B. Thus, for the example when the bottom side BS of the beam 7810 (and the hard stop structure 7900) is in compression, these stop surfaces (which function as the compression stop surfaces) contact each other to limit further displacement. As shown in FIG. 20C, when under tension, the surface 7952 of component 7950 contacts the surface 7942 of component 7940 and surface 7956 of component 7950 contacts surface 7966 of component 7960. The same corresponding surfaces of the other adjacent components (e.g., 7930 and 7970) can contact each other in the same manner. For example, surface 7946 of component 7940 can contact a corresponding surface of component 7930 as shown in FIG. 20C. Thus, for the example given when the top side TS of the beam 7810 (and the hard stop structure 7900) is in tension, these stop surfaces (which function as the tension stop surfaces) contact each other to limit further displacement. Additionally, when the bottom side BS of the beam 7810 is under compression, the tension stop surfaces on the bottom side are spaced apart from each other, and when the top side TS of the beam 7810 is under tension, the compression stop surfaces on the top side are spaced apart from each other.

When the surfaces of the components 7920 contact each other, further displacement of the hard stop structure 7900 (and beam 7810) is prevented. Thus, the contacting surfaces of the components 7920 function as stop surfaces to prevent the hard stop structure 7900 and the beam 7810 from further displacement or bending. In this embodiment, the interlocking components 7920 extend about the circumference of the hard stop structure 7900 and therefore provide stop surfaces at various locations about the circumference of the hard stop structure 7900. With this configuration, the interlocking components 7920 can limit the displacement of the hard stop structure 7900 (and beam 7810) in all directions of lateral forces imparted on the hard stop structure 7900 (i.e., lateral forces in the X-direction, the Y-direction, or having any component in the X- or Y-direction). Thus, when a force F (as shown in FIG. 13B) is imparted on the distal end of the medical device 7400, causing the hard stop structure 7900 and beam 7810 to bend, interlocking components on both the top side TS and bottom side BS of the hard stop structure 7900 can engage (i.e., the opposing surfaces of the interlocking components contact each other) to prevent further bending or displacing on both the compression side and the tension side of the hard stop structure 7900 (and beam 7810). Thus, in this embodiment, the hard stop structure 7900 provides a reactive moment instead of a single reactive force once the hard stop surfaces engage.

Although the above description of the function of the hard stop structure 7900 describes only components 7930, 7940, 7950, 7960 and 7970, it should be understood that the hard stop structure 7900 includes multiple interlocking components 7920, as shown, for example, in FIGS. 19A and 19B. Thus, as the beam 7810 and hard stop 7900 bend, various stop surfaces of the components 7920 will contact each other around the circumference of the hard stop structure 7900 depending on the direction of the force imparted on the medical device. Additionally, although each component (e.g., component 7940) is shown as including two compression stop surfaces (e.g., surfaces 7941, 7948) and two tension stop surfaces (e.g., surfaces 7942, 7946), in other embodiments each component can have any number of stop surfaces that engage with corresponding stop surfaces to limit bending.

In this embodiment, the opening 7935 defines multiple interlocking components that wrap about a circumference of the hard stop structure in a spiral pattern. The spiral pattern is accommodated by the asymmetry of the shape of the interlocking components 7920. Specifically, the surfaces 7947 and 7949 are not stop surfaces, but are instead substantially parallel to the Z-axis and do not contact their adjacent surfaces during either compression or tension. Moreover, the surface 7947 is longer than the surface 7949, which causes the component 7940 to be asymmetrical. This causes the interlocking components 7920 to wrap about a circumference of the hard stop structure in a spiral pattern. The difference in length between the surfaces 7947 and 7949 determines the angle of the pattern (relative to the center axis C-A of the shaft 7410 and/or the center axis $A_B$ of the beam 7810). For example, although the spiral angle Θ of the opening 7935 is between about 85 and 90 degrees (see FIG. 19A), in other embodiments, increasing the difference in length between the surface 7947 and the surface 7949 can result in smaller spiral angles (e.g., between 75 and 85 degrees; between 60 and 75 degrees). In an alternative embodiment, a hard stop structure can include multiple individual openings (e.g., "rings") that each wrap about a circumference of the hard stop structure instead of a continuous spiral pattern.

In addition to producing contacting stop surfaces on both the top side TS of the hard stop structure 7900 and the bottom side BS of the hard stop structure 7900, the multiple revolutions of the interlocking components 7920 also produces additional points of contact at different locations along the center axis $A_B$ of the beam 7810. The multiple revolutions also allows for a greater amount of deflection of the hard stop structure 7900. For example, each set of interlocking components 7920 allows an amount of bend of the beam 7810 equal to the size (e.g., width) of the opening 7935. Thus, a greater number of revolutions of the opening 7935 around the hard stop structure 7900, allows for a greater amount of bending of the beam 7810.

Figure 21:
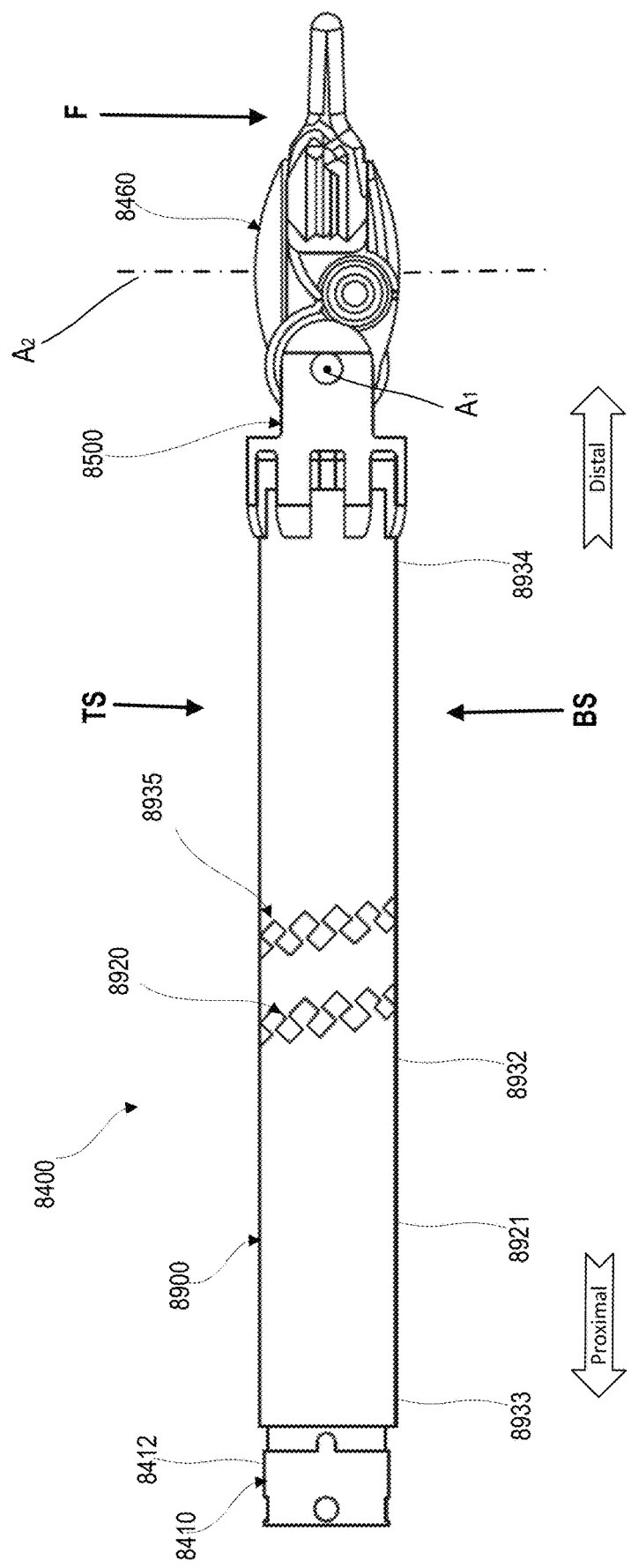
FIG. 21 is a side view of a portion of a medical device, according to another embodiment.

Although the hard stop structure 7900 is shown as defining an opening 7935 that extends about the circumference of the hard stop structure 7900 by about eight revolutions, in other embodiments, a hard stop structure can define an opening (or can include a set of interlocking components) that extends any number of revolutions about the circumference. For example, a hard stop structure can define an opening that extends about the circumference of the hard stop 2, 3, 4, 5, 6, etc. revolutions. For example, FIG. 21 is a side view of a portion of a medical instrument 8400, according to another embodiment. In some embodiments, the instrument 8400 or any of the components therein are optionally parts of a surgical system that performs surgical procedures, and which can include a manipulator unit, a series of kinematic linkages, a series of cannulas, or the like. The instrument 8400 (and any of the instruments described herein) can be used in any suitable surgical system, such as the MIRS system 1000 shown and described above.

The instrument 8400 can include a mechanical structure (not shown), a shaft 8410, a hard stop structure 8900, a force sensor unit (not shown) including a beam and one or more strain sensors disposed on the beam, a wrist assembly 8500, and an end effector 8460. The shaft 8410, force sensor unit, wrist assembly 8500 and end effector 8460 can be constructed the same as or similar to and function the same as or similar to the like components in other embodiments described herein and are therefore not described in detail with respect this embodiment. Although not shown, the instrument 8400 can also include a number of cables that couple the mechanical structure to the wrist assembly 8500 and end effector 8460. The instrument 8400 is configured such that select movements of the cables produces rotation of the wrist assembly 8500 (i.e., pitch rotation) about a first axis of rotation $A_1$ (which functions as a pitch axis, the term pitch is arbitrary), yaw rotation of the end effector 8460 about a second axis of rotation $A_2$ (which functions as the yaw axis, the term yaw is arbitrary), a cutting rotation of the tool members of the end effector 8460 about the second axis of rotation $A_2$, or any combination of these movements. Changing the pitch or yaw of the instrument 8400 can be performed by manipulating the cables in a similar manner as described above for medical instrument 7400.

The various components of the medical device 8400 can be configured the same as or similar to, and function the same as or similar to, similar components described above for previous embodiments and therefore are not described in detail with reference to this embodiment. For example, in this embodiment, the hard stop structure 8900 is tubular or cylindrical, and includes an opening 8935 in a wall 8921 of the hard stop structure 8900. The opening 8935 can be formed into the hard stop structure 8900 by any suitable methods, such as, for example, laser cut, electronic discharge machining, or the like. In some embodiments, the hard stop structure can be a laser-cut tube. The opening 8935 defines multiple interlocking components 8920 having opposing stop surfaces. In this embodiment, the opening 8935 extends about the circumference of the hard stop structure 8900 two revolutions in a spiral pattern. The hard stop structure 8900 includes a proximal end portion 8933, a distal end portion 8934, and a middle portion 8932 between the proximal end portion 8933 and the distal end portion 8934. The hard stop structure 8900 defines an interior lumen (not shown) within which the beam is disposed.

As shown in FIG. 21, the proximal end portion 8933 of the hard stop structure 8900 is coupled to the shaft 8410 and the distal end portion 8934 of the hard stop structure 8900 is coupled to the wrist assembly 8500. The proximal end portion 8933 can be fixedly coupled to a distal end portion 8412 of the shaft 8410 and the distal end portion 8934 can be coupled to the wrist assembly 8500 by any suitable mechanism, such as, for example, by a weld or an adhesive. In this manner, displacement of the wrist assembly 8500 relative to the shaft 8410 will cause displacement of the distal end portion 8934 of the hard stop structure 8900 relative to the proximal end portion 8933 of the hard stop structure 8900.

The multiple interlocking components 8920 formed by the opening 8935 define a repeating pattern within the wall 8921 of the hard stop structure 8900 about the circumference of the hard stop structure 8900. In this manner, the hard stop structure 7900 can limit the range of motion (i.e., bending) of the hard stop structure 8900 and the beam 8810 in all directions lateral to the Z axis, and not just only in the X direction or Y direction. Each of the interlocking components 8920 includes multiple surfaces that contact corresponding surfaces of adjacent interlocking components in certain instances when a motion limit has been reached as described above for the previous embodiment.

In use, the end effector 8460 contacts anatomical tissue, which may result in X, Y, or Z direction forces (see e.g., FIG. 13B described above for medical device 7400) being imparted on the end effector 8460 and that may also result in moment forces about the various axes. The strain sensors (not shown) can be used to measure strain in the beam (not shown) as a result of such forces imparted on the end effector 8460. More specifically, the strain sensors 7830 can measure forces imparted on the end effector 8460 that are transverse (e.g., perpendicular) to the center axis $A_B$ of the beam as such forces are transferred to the beam in the X and Y directions. Specifically, the transverse forces acting upon the end effector 8460 can cause a slight bending of the beam, which can result in a tensile strain imparted to one side of the beam and a compression strain imparted to the opposite side of the beam. As with the previous embodiments, the strain sensors are coupled to the beam to measure such tensile and compression forces.

As described above for previous embodiments, the hard stop structure 8900 can limit the displacement of the beam 8810 relative to a center axis (not shown in FIG. 21) of the shaft 8410 and/or relative to a center axis (not shown in FIG. 21) of the beam when a strain in the beam exceeds a preset amount or when the beam bends or is displaced a preset amount (e.g., preset bending angle). More specifically, when a force F is imparted on a distal portion of the medical device 8400 (e.g., at end effector 8460) in the X or Y directions (see FIG. 13C for reference to X, Y and Z directions), such transverse force can cause bending the beam to bend (about either or some combination of the X axis or the Y axis), which can result in a tensile strain imparted to one side of the beam and a compression strain imparted to the opposite side of the beam. The strain sensors on the beam can measure such tensile and compression strains. For example, in this example embodiment, with the force F, the hard stop structure 8900 and beam would bend downward such that a tensile strain would be imparted on a top side TS of the beam and a compression strain would be imparted on a bottom side BS of the beam.

As described above for previous embodiments, as the beam bends, specific surfaces of the interlocking components 8920 are configured to engage each other when the beam bends to a desired preset bending angle or is otherwise displaced to a preset amount. Thus, the surfaces of the interlocking components 8920 function as stop surfaces to prevent the hard stop structure 8900 and beam from bending (or being displaced any further). When the surfaces of the components 8920 contact each other, further displacement of the hard stop structure 8900 (and beam) is prevented. Thus, the contacting surfaces of the components 8920 function as stop surfaces to prevent the hard stop structure 8900 and the beam from further displacement or bending. In this embodiment, the interlocking components 8920 extend about the circumference of the hard stop structure 8900 and therefore provide stop surfaces at various locations about the circumference of the hard stop structure 8900. With this configuration, the interlocking components 8920 can limit the displacement of the hard stop structure 8900 (and beam) in all directions of lateral forces imparted on the hard stop structure 8900 (i.e., lateral forces in the X-direction, the Y-direction, or having any component in the X- or Y-direction). Thus, when a force F (as shown in FIG. 21) is imparted on the distal end of the medical device 8400, causing the hard stop structure 8900 and beam to bend, interlocking components on both the top side TS and bottom side BS of the hard stop structure 8900 can engage (i.e., the opposing surfaces of the interlocking components contact each other) to prevent further bending or displacing on both the compression side and the tension side of the hard stop structure 8900 (and beam). Thus, as with the previous embodiment, the hard stop structure 8900 provides a reactive moment instead of a single reactive force once the hard stop surfaces engage.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the components of a surgical instrument as described herein can be constructed from any material, such as medical grade stainless steel, nickel alloys, titanium alloys or the like. Further, any of the links, tool members, beams, shafts, cables, or other components described herein can be constructed from multiple pieces that are later joined together. For example, in some embodiments, a link can be constructed by joining together separately constructed components. In other embodiments however, any of the links, tool members, beams, shafts, cables, or components described herein can be monolithically constructed.

Although the instruments are generally shown as having an axis of rotation of the tool members (e.g., axis $A_2$) that is normal to an axis of rotation of the wrist member (e.g., axis $A_1$), in other embodiments any of the instruments described herein can include a tool member axis of rotation that is offset from the axis of rotation of the wrist assembly by any suitable angle.

Although some embodiments show strain sensors (e.g., 830, 2830, 3830, 4830) as being on a single side of the beam (e.g., 810, 2810, 3810, 4810) and other embodiments show strain sensors (e.g., 7830) on multiple sides of the beam (e.g., 7810), it should be understood that any of the embodiments can include one or more strain sensors on either a single side of the beam or on multiple sides of the beam. Further examples of an instrument with strain sensors on a single side of the beam are shown in International Patent Application No. PCT/US2020/060636, filed Nov. 15, 2020, which is incorporated herein by reference.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:
1. A medical device comprising:
a shaft comprising a distal end portion;
a beam comprising a proximal end portion and a distal end portion, the proximal end portion of the beam being coupled to the distal end portion of the shaft;
a link coupled to the distal end portion of the beam;
a strain sensor on the beam; and
a hard stop structure comprising a proximal end portion and a distal end portion, the proximal end portion of the hard stop structure being coupled to the distal end portion of the shaft, and the distal end portion of the hard stop structure being coupled to the link;

the hard stop structure comprising a first interlocking component and a second interlocking component, the first interlocking component having a first stop surface and a second stop surface, the second interlocking component having a third stop surface and a fourth stop surface, the first stop surface being nonparallel to the second stop surface, the third stop surface being nonparallel to the fourth stop surface;

wherein the first interlocking component and the second interlocking component are positioned to limit a range of motion of the distal end portion of the beam with reference to the proximal end portion of the beam in a first direction by the first stop surface contacting the third stop surface.

2. The medical device of claim 1, wherein:
the and
the first interlocking component and the second interlocking component are positioned to limit the range of motion of the distal end portion of the beam with reference to the proximal end portion of the beam in a second direction opposite the first direction by the second stop surface contacting the fourth stop surface.

3. The medical device of claim 2, wherein:
the first interlocking component and the second interlocking component are located on a first side of the beam.

4. The medical device of claim 1, wherein:
the hard stop structure comprises a third interlocking component and a fourth interlocking component, the third interlocking component having a first stop surface and a second stop surface, the fourth interlocking component having a third stop surface and a fourth stop surface, the first stop surface of the third interlocking component being nonparallel to the second stop surface of the third interlocking component, the third stop surface of the fourth interlocking component being nonparallel to the fourth stop surface of the fourth interlocking component;
the third interlocking component and the fourth interlocking component are located on an opposite side of the beam than the first interlocking component and the second interlocking component; and
the third interlocking component and the fourth interlocking component are positioned to limit the range of motion of the distal end portion of the beam with reference to the proximal end portion of the beam in the first direction by the first stop surface of the third interlocking component contacting the third stop surface of the fourth interlocking component.

5. The medical device of claim 1, wherein:
the hard stop structure comprises a wall; and
the first stop surface, the second stop surface, the third stop surface and the fourth stop surface are formed in the wall of the hard stop structure.

6. The medical device of claim 1, wherein:
the hard stop structure comprises a laser-cut tube in which the first stop surface, the second stop surface, the third stop surface and the fourth stop surface are defined.

7. The medical device of claim 4, wherein:
the hard stop structure comprises a laser-cut tube in which the first stop surface and the second stop surface of the first interlocking component and the first stop surface and the second stop surface of the third interlocking component are defined by a single laser cut; and
the single laser cut extends in a spiral about the laser-cut tube.

8. The medical device of claim 1, wherein:
the medical device comprises an end effector mechanism; and
the end effector mechanism comprises the link.

9. The medical device of claim 1, wherein:
the medical device comprises a wrist mechanism; and
the wrist mechanism comprises the link.

10. A medical device comprising:
a shaft comprising a proximal end portion, a distal end portion, and a center axis defined between the proximal end portion and the distal end portion;
a beam comprising a proximal end portion and a distal end portion, the proximal end portion of the beam being coupled to the distal end portion of the shaft;
a link coupled to the distal end portion of the beam;
a strain sensor on the beam, the strain sensor being configured to produce a signal associated with a strain in the beam that results when a force is exerted on the link; and
a hard stop structure comprising a proximal end portion, a distal end portion, a wall, and a lumen between the proximal end portion of the hard stop structure and the distal end portion of the hard stop structure,
the proximal end portion of the hard stop structure being coupled to the distal end portion of the shaft,
the distal end portion of the hard stop structure being coupled to the link,
the beam being at least partially within the lumen,
the hard stop structure comprising a plurality of interlocking components on the wall of the hard stop structure, each interlocking component of the plurality of interlocking components comprising a first stop surface and a second stop surface nonparallel to the first stop surface; and
the plurality of interlocking components being positioned to limit a displacement of the beam relative to the center axis when the strain in the beam exceeds a preset amount.

11. The medical device of claim 10, wherein:
the plurality of interlocking components is formed by an opening defined by the wall of the hard stop structure.

12. The medical device of claim 10, wherein:
the hard stop structure has a cylindrical shape;
the plurality of interlocking components is formed by an opening defined by the wall of the hard stop structure; and
the opening extends circumferentially around the wall by more than one revolution.

13. The medical device of claim 12, wherein:
the opening forms a spiral of at least two revolutions.

14. The medical device of claim 10, wherein:
the hard stop structure comprises a first circumferential side and a second circumferential side opposite the first circumferential side;
the plurality of interlocking components comprises a first interlocking component, a second interlocking component, a third interlocking component and a fourth interlocking component;
the first interlocking component and the second interlocking component are on the first circumferential side of the hard stop structure and the first stop surface of the first interlocking component contacts the first stop surface of the second interlocking component when the hard stop structure is displaced by a threshold displacement; and
the third interlocking component and the fourth interlocking component are on the second circumferential side of the hard stop structure and the first stop surface of the third interlocking component contacts the first stop surface of the fourth interlocking component when the hard stop structure is displaced by the threshold displacement.

15. The medical device of claim 14, wherein:
the first circumferential side of the hard stop structure is in tension when the hard stop structure is displaced by the threshold displacement; and
the second circumferential side of the hard stop structure is in compression when the hard stop structure is displaced by the threshold displacement.

16. The medical device of claim 10, wherein:
the hard stop structure comprises a circumferential side;
the plurality of interlocking components comprises a first interlocking component on the circumferential side and a second interlocking component on the circumferential side;
the first interlocking component interlocks with the second interlocking component;
the first stop surface of the first interlocking component is in contact with the first stop surface of the second interlocking component when the force produces tension on the circumferential side of the hard stop structure; and
the second stop surface of the first interlocking component is in contact with the second stop surface of the second interlocking component when the force produces compression on the circumferential side of the hard stop structure.

17. The medical device of claim 16, wherein:
the second stop surface of the first interlocking component is spaced apart from the second stop surface of the second interlocking component when the force produces tension on the circumferential side of the hard stop structure; and
the first stop surface of the first interlocking component is spaced apart from the first stop surface of the second interlocking component when the force produces compression on the circumferential side of the hard stop structure.

18. The medical device of claim 10, wherein:
the plurality of interlocking components produces a reactive moment when the hard stop structure is displaced by a preset bending angle.

19. The medical device of claim 10, wherein:
the strain sensor is a first strain sensor coupled to the beam at a location near the proximal end portion of the beam; and
the medical device comprises a second strain sensor coupled to the beam at a location near the distal end portion of the beam.

\* \* \* \* \*

UNITED STATES PATENT AND TRADEMARK OFFICE
CERTIFICATE OF CORRECTION

PATENT NO. : 12,239,393 B2  
APPLICATION NO. : 17/322276  
DATED : March 4, 2025  
INVENTOR(S) : Zhou Ye et al.

Page 1 of 1

It is certified that error appears in the above-identified patent and that said Letters Patent is hereby corrected as shown below:

In the Claims

Column 31, Lines 15-17 (Claim 2): the phrase "wherein: the and the first" should be – wherein: the first –

Signed and Sealed this  
Fifteenth Day of April, 2025

Coke Morgan Stewart  
*Acting Director of the United States Patent and Trademark Office*